United States Patent
Maragakis

(10) Patent No.: US 11,717,506 B2
(45) Date of Patent: Aug. 8, 2023

(54) NEUROPROTECTIVE COMPOUNDS FOR AMYOTROPHIC LATERAL SCLEROSIS

(71) Applicant: THE JOHNS HOPKINS UNIVERSITY, Baltimore, MD (US)

(72) Inventor: Nicholas J. Maragakis, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 225 days.

(21) Appl. No.: 16/868,764

(22) Filed: Jul. 1, 2020

(65) Prior Publication Data

US 2020/0352902 A1    Nov. 12, 2020

Related U.S. Application Data

(60) Provisional application No. 62/844,649, filed on May 7, 2019.

(51) Int. Cl.
*A61K 31/353* (2006.01)
*A61P 25/28* (2006.01)

(52) U.S. Cl.
CPC ............ *A61K 31/353* (2013.01); *A61P 25/28* (2018.01)

(58) Field of Classification Search
CPC ............................. A61K 31/353; A61P 25/28
See application file for complete search history.

(56) References Cited

U.S. PATENT DOCUMENTS

| | | | |
|---|---|---|---|
| 5,399,363 A | 3/1995 | Liversidge et al. | |
| 5,466,468 A | 11/1995 | Schneider et al. | |
| 5,543,158 A | 8/1996 | Gref et al. | |
| 5,580,579 A | 12/1996 | Ruddy et al. | |
| 5,629,001 A | 5/1997 | Michael et al. | |
| 5,641,515 A | 6/1997 | Ramtoola | |
| 5,725,871 A | 3/1998 | Illum | |
| 5,756,353 A | 5/1998 | Debs | |
| 5,780,045 A | 7/1998 | McQuinn et al. | |
| 5,792,451 A | 8/1998 | Sarubbi et al. | |
| 5,804,212 A | 9/1998 | Illum | |
| 6,613,308 B2 | 9/2003 | Bartus et al. | |
| 6,737,514 B1 | 5/2004 | Wang et al. | |
| 9,499,510 B2* | 11/2016 | Savory | A61P 25/00 |
| 2014/0275068 A1 | 9/2014 | Savory et al. | |
| 2016/0318891 A1 | 11/2016 | Savory et al. | |
| 2017/0258758 A1 | 9/2017 | Massague et al. | |

FOREIGN PATENT DOCUMENTS

CA    2958879    2/2016

OTHER PUBLICATIONS

Almad et al., Connexin 43 in astrocytes contributes to motor neuron toxicity in amyotrophic lateral sclerosis. Glia. Jul. 2016;64(7):1154-69.
Boulting et al., A functionally characterized test set of human induced pluripotent stem cells. Nat Biotechnol. Mar. 2011;29(3):279-86.
Bradley et al., Diffusion-weighted MRI used to detect in vivo modulation of cortical spreading depression: comparison of sumatriptan and tonabersat. Exp Neurol. Dec. 2001;172(2):342-53.
Bruijn et al., ALS-linked SOD1 mutant G85R mediates damage to astrocytes and promotes rapidly progressive disease with SOD1-containing inclusions. Neuron. Feb. 1997;18(2):327-38.
Chan et al., Identification of (−)-cis-6-acetyl-4S-(3-chloro-4-fluoro-benzoylamino)-3,4-dihydro-2,2-dimethyl-2H-benzo[b]pyran-3S-ol as a potential antimigraine agent. Bioorg Med Chem Lett 9, 1999, 285-290.
Chen et al., Carcinoma-astrocyte gap junctions promote brain metastasis by cGAMP transfer. Nature. May 26, 2016;533(7604):493-498.
Chew et al., Role of connexin43 in central nervous system injury. Exp Neurol. Oct. 2010;225(2):250-61.
Chio et al., The Role of APOE in the Occurrence of Frontotemporal Dementia in Amyotrophic Lateral Sclerosis. JAMA Neurol. Apr. 2016;73(4):425-30.
Christ et al., Gap junction-mediated intercellular diffusion of Ca2+ in cultured human corporal smooth muscle cells. Am J Physiol. Aug. 1992;263(2 Pt 1):C373-83.
Clement et al., Wild-type nonneuronal cells extend survival of SOD1 mutant motor neurons in ALS mice. Science. Oct. 3, 2003;302(5642):113-7.
Dahlof et al., Efficacy and safety of tonabersat, a gap-junction modulator, in the acute treatment of migraine: a double-blind, parallel-group, randomized study. Cephalalgia., 2009, 29 Suppl 2, pp. 7-16.
Damodaram et al., Tonabersat inhibits trigeminal ganglion neuronal-satellite glial cell signaling. Headache. Jan. 2009;49(1):5-20.
Davidson et al., Connexin hemichannel blockade improves outcomes in a model of fetal ischemia. Ann Neurol. Jan. 2012;71(1):121-32.
Di Giorgio et al., Non-cell autonomous effect of glia on motor neurons in an embryonic stem cell-based ALS model. Nat Neurosci. May 2007;10(5):608-14.
Diaz-Amarilla et al., Phenotypically aberrant astrocytes that promote motoneuron damage in a model of inherited amyotrophic lateral sclerosis. Proc Natl Acad Sci U S A. Nov. 1, 2011;108(44):18126-31.

(Continued)

*Primary Examiner* — Timothy R Rozof
(74) *Attorney, Agent, or Firm* — Kelly A. Barton; Casimir Jones, S.C.

(57) ABSTRACT

Described are methods for treating or preventing a neurological disease in a subject. The methods include administering a suppressor of hemichannel permeability to a subject having or prone of getting a neurological disease. The methods include the treatment and prevention of amyotrophic lateral sclerosis (ALS).

27 Claims, 7 Drawing Sheets

Specification includes a Sequence Listing.

(56) References Cited

OTHER PUBLICATIONS

Durham et al., Neurological mechanisms of migraine: potential of the gap-junction modulator tonabersat in prevention of migraine. Cephalalgia. Nov. 2009;29 Suppl 2(Suppl 2):1-6.
Emde et al., Dysregulated miRNA biogenesis downstream of cellular stress and ALS-causing muations: a new mechanism for ALS. EMBO J. 2015, 34(21), pp. 263-2651.
Endo et al., Astrocytic TGF-β1: detrimental factor in ALS. Oncotarget. Jun. 30, 2015;6(18):15728-9.
Giaume et al., Pharmacological and genetic approaches to study connexin-mediated channels in glial cells of the central nervous system. Brain Res Rev. May 2010;63(1-2):160-76.
Goadsby et al., Randomized, double-blind, placebo-controlled, proof-of-concept study of the cortical spreading depression inhibiting agent tonabersat in migraine prophylaxis. Cephalalgia. Jul. 2009;29(7):742-50.
Goldberg et al., Selective transfer of endogenous metabolites through gap junctions composed of different connexins. Nat Cell Biol. Nov. 1999;1(7):457-9.
Guo et al., Sensory involvement in the SOD1-G93A mouse model of amyotrophic lateral sclerosis. Exp Mol Med. Mar. 31, 2009;41(3):140-50.
Haidet-Phillips et al., Astrocytes from familial and sporadic ALS patients are toxic to motor neurons. Nat Biotechnol. Aug. 10, 2011;29(9):824-8.
Hall et al., Relationship of microglial and astrocytic activation to disease onset and progression in a transgenic model of familial ALS. Glia. Jul. 1998;23(3):249-56.
Hauge et al., Effects of tonabersat on migraine with aura: a randomised, double-blind, placebo-controlled crossover study. Lancet Neurol. Aug. 2009;8(8):718-23.
Herdon et al., Characterization of the binding of [3H]-SB-204269, a radiolabelled form of the new anticonvulsant SB-204269, to a novel binding site in rat brain membranes. Br J Pharmacol. Aug. 1997;121(8):1687-91.
Howland et al., Focal loss of the glutamate transporter EAAT2 in a rat model of SOD1 mutant-mediated amyotrophic lateral sclerosis (ALS). Proc Natl Acad Sci U S A. Feb. 5, 2002;99(3):1604-9.
Huang et al., Critical role of connexin 43 in secondary expansion of traumatic spinal cord injury. J Neurosci. Mar. 7, 2012;32(10):3333-8.
Hwang et al., Gastric retentive drug-delivery systems. Crit Rev Ther Drug Carrier Syst. 1998;15(3):243-84.
Kato et al., Absence of SOD1 gene abnormalities in familial amyotrophic lateral sclerosis with posterior column involvement without Lewy-body-like hyaline inclusions. Acta Neuropathol. Nov. 1996;92(5):528-33.
Keller et al., Treatment with minocycline after disease onset alters astrocyte reactivity and increases microgliosis in SOD1 mutant mice. Exp Neurol. Mar. 2011;228(1):69-79.
Kerr et al., High pressure-induced retinal ischaemia reperfusion causes upregulation of gap junction protein connexin43 prior to retinal ganglion cell loss. Exp Neurol. Mar. 2012;234(1):144-52.
Kim et al., Tonabersat Prevents Inflammatory Damage in the Central Nervous System by Blocking Connexin43 Hemichannels. Neurotherapeutics. Oct. 2017;14(4):1148-1165.
Konietzko et al., Astrocytic dye coupling in rat hippocampus: topography, developmental onset, and modulation by protein kinase C. Hippocampus. Jun. 1994;4(3):297-306.
Lawrence et al., Transmission of hormonal stimulation by cell-to-cell communication. Nature. Apr. 6, 1978;272(5653):501-6.
Lee et al., Glial and neuronal connexin expression patterns in the rat spinal cord during development and following injury. J Comp Neurol. Aug. 15, 2005;489(1):1-10.
Lepore et al., Focal transplantation-based astrocyte replacement is neuroprotective in a model of motor neuron disease. Nat Neurosci. Nov. 2008;11(11):1294-301.

MacKenzie et al., The role of transactive response DNA-binding protein-43 in amyotrophic lateral sclerosis and frontotemporal dementia. Curr Opin Neurol. Dec. 2008;21(6):693-700.
Marchetto et al., Non-cell-autonomous effect of human SOD1 G37R astrocytes on motor neurons derived from human embryonic stem cells. Cell Stem Cell. Dec. 4, 2008;3(6):649-57.
Mathiowitz et al., Biologically erodable microspheres as potential oral drug delivery systems. Nature. Mar. 27, 1997;386(6623):410-4.
Mei et al., Astroglial connexin immunoreactivity is specifically altered at β-amyloid plaques in β-amyloid precursor protein/ presenilin1 mice. Neuroscience. Nov. 24, 2010;171(1):92-105.
Mulligan et al., Calcium transients in astrocyte endfeet cause cerebrovascular constrictions. Nature. Sep. 9, 2004;431(7005):195-9.
Musil et al., Multisubunit assembly of an integral plasma membrane channel protein, gap junction connexin43, occurs after exit from the ER. Cell. Sep. 24, 1993;74(6):1065-77.
Nagai et al., Astrocytes expressing ALS-linked mutated SOD1 release factors selectively toxic to motor neurons. Nat Neurosci. May 2007;10(5):615-22.
Orellana et al., Modulation of brain hemichannels and gap junction channels by pro-inflammatory agents and their possible role in neurodegeneration. Antioxid Redox Signal. Feb. 2009;11(2):369-99.
Qu et al., Function of the voltage gate of gap junction channels: selective exclusion of molecules. Proc Natl Acad Sci U S A. Jan. 22, 2002;99(2):697-702.
Rash et al., Identification of cells expressing Cx43, Cx30, Cx26, Cx32 and Cx36 in gap junctions of rat brain and spinal cord. Cell Commun Adhes. 2001;8(4-6):315-20.
Read et al., SB-220453, a potential novel antimigraine agent, inhibits nitric oxide release following induction of cortical spreading depression in the anaesthetized cat. Cephalalgia. Mar. 2000;20(2):92-9.
Rothstein et al., Selective loss of glial glutamate transporter GLT-1 in amyotrophic lateral sclerosis. Ann Neurol. Jul. 1995;38(1):73-84.
Rouach et al., Astroglial metabolic networks sustain hippocampal synaptic transmission. Science. Dec. 5, 2008;322(5907):1551-5.
Roybon et al., Human stem cell-derived spinal cord astrocytes with defined mature or reactive phenotypes. Cell Rep. Sep. 12, 2013;4(5):1035-1048.
Saez et al., Hepatocyte gap junctions are permeable to the second messenger, inositol 1,4,5-trisphosphate, and to calcium ions. Proc Natl Acad Sci U S A. Apr. 1989;86(8):2708-12.
Schiffer et al., Synaptic vesicle proteins, synaptophysin and chromogranin A in amyotrophic lateral sclerosis. J Neurol Sci. May 1995;129 Suppl:68-74.
Spray et al., Functional connexin "hemichannels": a critical appraisal. Glia. Nov. 15, 2006;54(7):758-73.
Tabernero et al., Endothelin-1 regulates glucose utilization in cultured astrocytes by controlling intercellular communication through gap junctions. Glia. Mar. 1996;16(3):187-95.
Taga et al., Role of Human-Induced Pluripotent Stem Cell-Derived Spinal Cord Astrocytes in the Functional Maturation of Motor Neurons in a Multielectrode Array System. Stem Cells Transl Med. Dec. 2019;8(12):1272-1285.
Takenaga et al., Microparticle resins as a potential nasal drug delivery system for insulin. J Control Release. Mar. 2, 1998;52(1-2):81-7.
Theis et al., General and conditional replacement of connexin43-coding DNA by a lacZ reporter gene for cell-autonomous analysis of expression. Cell Commun Adhes. 2001;8(4-6):383-6.
Tvedskov et al., A double-blind study of SB-220453 (Tonerbasat) in the glyceryltrinitrate (GTN) model of migraine. Cephalalgia. Oct. 2004;24(10):875-82.
Upton et al., Benzo[b]pyranols and related novel antiepileptic agents. Prog Med Chem. 2000;37:177-200.
Upton et al., Profile of SB-204269, a mechanistically novel anticonvulsant drug, in rat models of focal and generalized epileptic seizures. Br J Pharmacol. Aug. 1997;121(8):1679-86.
Voelker. Antioxidant Drug Approved for ALS. JAMA. Jun. 20, 2017;317(23):2363.
Wallraff et al., The impact of astrocytic gap junctional coupling on potassium buffering in the hippocampus. J Neurosci. May 17, 2006;26(20):5438-47.

(56) References Cited

OTHER PUBLICATIONS

Yamanaka et al., Astrocytes as determinants of disease progression in inherited amyotrophic lateral sclerosis. Nat Neurosci. Mar. 2008;11(3):251-3.

Yi et al., Astroglial connexin43 contributes to neuronal suffering in a mouse model of Alzheimer's disease. Cell Death Differ. Oct. 2016;23(10):1691-701.

Zong et al., Gap junction mediated miRNA intercellular transfer and gene regulation: A novel mechanism for intercellular genetic communication. Sci Rep. Jan. 27, 2016;6:19884.

* cited by examiner

SEQUENCE LISTING

```
<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 1

Lys Gln Ile Glu Ile Lys Lys Phe Lys
1               5

<210> SEQ ID NO 2
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 2
```

```
Tyr Gly Arg Lys Lys Arg Arg Gln Arg Arg Arg Lys Gln Ile Glu Ile
1               5                   10                  15
Lys Lys Phe Lys
            20
```

NEUROPROTECTIVE COMPOUNDS FOR AMYOTROPHIC LATERAL SCLEROSIS

REFERENCE TO RELATED APPLICATIONS

This application claims the benefit of U.S. Provisional Patent Application No. 62/844,649, filed on May 7, 2019, which is hereby incorporated by reference for all purposes as if fully set forth herein.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on May 6, 2020, is named P15316-02_ST25.txt and is 745 bytes in size.

BACKGROUND OF THE INVENTION

Tonabersat (SB-220453), a novel cis benzopyran derivative, was selected for its effect at moderating abnormally high levels of neuronal excitability. Tonabersat was shown to reduce neurogenic extravasation of plasma protein in the meninges, a mechanism important to the pathophysiology of migraine headaches. In addition, it was shown to antagonize cortical spreading depression[1]. The mechanism behind the reduction in cortical spreading depression is in part related to a reduction in nitric oxide release[2]. Cortical spreading depression is believed to play a key role in migraine with aura[3]. Based upon this hypothesis and preclinical results, tonabersat underwent study in phase II clinical trials as a prophylaxis for migraine[4,5]. In the study by Hauge and colleagues, tonabersat showed a preventive effect on attacks of migraine aura but no efficacy on non-aura attacks. It was also found to be well tolerated[4].

One mechanism by which cortical spreading depression is thought to occur is through gap junction and hemichannel mediated cell-cell signaling[6]. When using tonabersat to block connexin 43 (Cx43) gap junctions, it was found that this compound inhibited dye transfer from astrocytes to cancer cells and the release of IFNα and TNF in astrocyte cancer cell co-cultures. Treatment with tonabersat also inhibited brain metastases in xenograft and immunocompetent models. Therefore, this compound could be of interest in inhibiting metastases to the braid.

While Amyotrophic Lateral Sclerosis (ALS) is a motor neuron disease, studies from chimeric mice with mosaic expression of wildtype (WT) and mutant SOD1 glia (particularly astrocytes) surrounding motor neurons (MNs) suggests that motor neuron death is a non-cell autonomous process resulting in ALS pathogenesis[9]. The presence of WT non-neuronal cells (likely astrocytes) in the vicinity of mutant SOD1 (mSOD1) MNs prevents toxicity to these neurons. Conversely, mSOD1 in non-neuronal cells can induce toxicity with ubiquitin deposition in nearby WT MNs[9]. Studies from post-mortem ALS patients and transgenic ALS disease models reveals the presence of reactive astrogliosis during disease course[10,11,12] and dramatic loss of the glutamate transporter GLT1[13,14]. A largely consistent theme in the present understanding of disease progression, after onset, in ALS suggest that astrocytes play a role in this progression.

Studies with selective reduction of mSOD1 from astrocytes using SOD1$^{G37R}$Lox/GFAP-Cre (astrocyte specific Cre) mice results in prolongation of disease duration, but has no effect on disease onset[15]. This has also been supported in several other studies[16]. The inventor's work has also suggested that glial progenitor cell transplantation and replacement of mutant SOD1 astrocytes by wildtype glial progenitors may actually be protective in slowing disease progression[17]. Recent studies have employed co-cultures of mouse or human embryonic stem cell (ESC)-derived MNs with mSOD1 astrocytes and observed selective destruction of MNs by toxic mutant astrocyte-secreted factors[18,19,20]. The inventor's work, implicates the astrocyte connexin, Cx43, as a mediator of MN toxicity[21]. Together, these experiments implicate astrocytic influences on MN death and suggest an astrocyte/motor neuron interplay in ALS disease progression.

SUMMARY OF THE INVENTION

In accordance with an embodiment, the present invention provides a method for treating or preventing a neurodegenerative disease in a subject in need thereof comprising administering to the subject an effective amount of a suppressor of hemichannel permeability.

In accordance with another embodiment, the present invention provides a method for treating Amyotrophic Lateral Sclerosis (ALS) in a subject in need thereof comprising administering to the subject an effective amount a suppressor of hemichannel permeability so as not to modulate gap junction permeability.

In accordance with a further embodiment, the present invention provides a method for treating ALS comprising administering to a subject in need thereof, an effective amount of a suppressor of connexin and/or pannexin permeability.

In accordance with a further embodiment, the present invention provides a method for treating ALS comprising administering to a subject in need thereof, an effective amount of Tonabersat, or a salt, solvate, derivative or prodrug thereof.

DETAILED DESCRIPTION OF THE INVENTION

Figure 1:
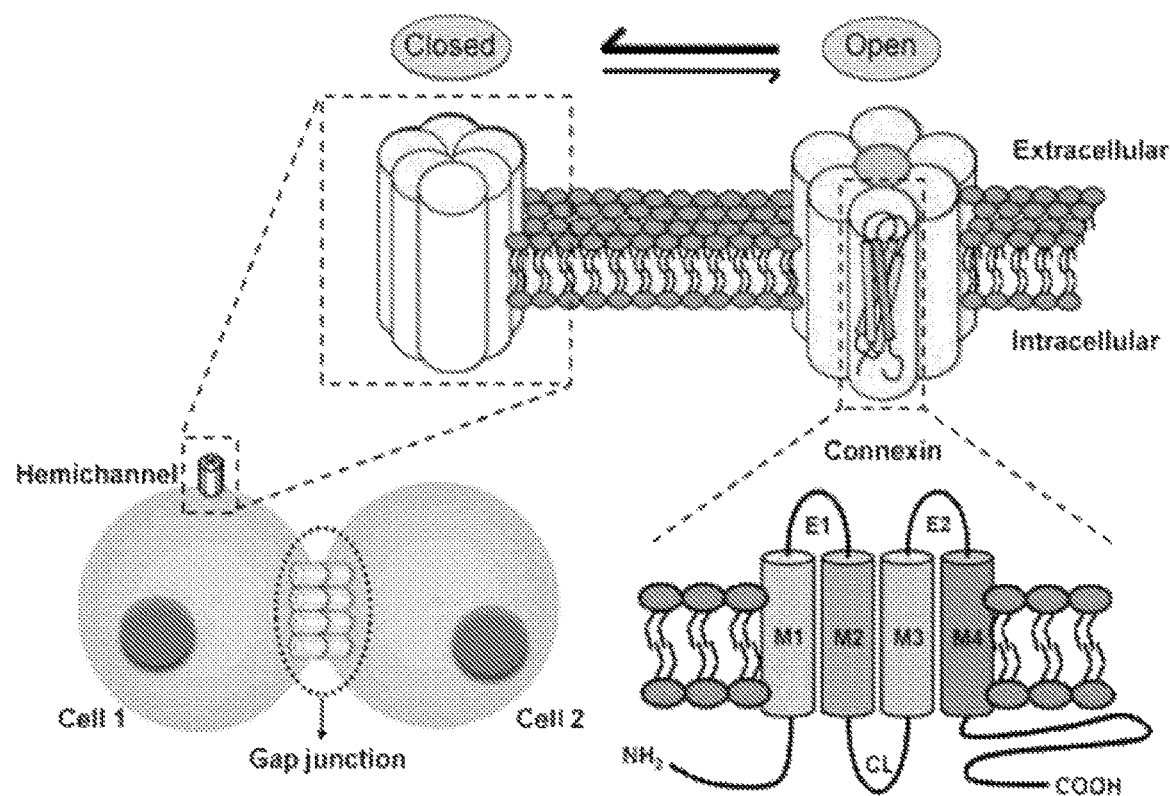
FIG. 1 illustrates the role of connexin in astrocytes.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The term "activity" refers to the ability of a gene to perform its function such as an enzyme catalyzing a reaction, or a hemichannel or gap junction, such as CX43, allowing the transfer of material across a membrane.

The term "agent" refers to any small molecule chemical compound (such as tonabersat), antibody, nucleic acid molecule, or polypeptide, or fragments thereof.

The term "ameliorate" refers to decrease, suppress, attenuate, diminish, arrest, or stabilize the development or progression of a disease such as amyotrophic lateral sclerosis.

The term "alteration" refers to a change (increase or decrease) in the expression levels or activity of a gene or polypeptide, hemichannel, or gap junction, as detected by standard art known methods such as those described herein. As used herein, an alteration includes a 10% change in expression levels, preferably a 25% change, more preferably a 40% change, and most preferably a 50% or greater change in expression levels."

The term "connexin" or "Cx" are transmembrane proteins that assemble to form vertebrate gap junctions or hemichannels. Connexins are commonly named according to their molecular weights, e.g. Cx26 is the connexin protein of 26 kDa. A competing nomenclature is the gap junction protein system, where connexins are sorted by their α (GJA) and β (GJB) forms, with additional connexins grouped into the C, D and E groupings, followed by an identifying number, e.g. GJA1 corresponds to Cx43.

The term "disease" refers to any condition or disorder that damages or interferes with the normal function of a cell, tissue, or organ. As used herein, the term includes motor neuron diseases (MNDs) which are a group of progressive neurological disorders that destroy motor neurons, the cells that control skeletal muscle activity such as walking, breathing, speaking, and swallowing. This group includes diseases such as amyotrophic lateral sclerosis, progressive bulbar palsy, primary lateral sclerosis, progressive muscular atrophy, spinal muscular atrophy, Kennedy's disease, and post-polio syndrome.

The term "effective amount" refers to the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "express" refers to the ability of a gene to express the gene product including for example its corresponding mRNA or protein sequence (s).

The term "gap junction" or "GJ" refers to intercellular connection between cells and they are located at the cell membrane. Each gap junction is composed of two hemichannels (one at each cell membrane) and when connected, allow a channel to form, connecting the cytoplasm of two cells. This gap junction forms a channel that allows various molecules, ions and electrical impulses to directly pass through a regulated gate between cells.

The term "hemichannel" or "HC" refers to half of a gap junction and allows communication from a cell's cytoplasm to the extracellular space.

The term, "obtaining" as in "obtaining an agent" includes synthesizing, purchasing, or otherwise acquiring the agent.

The term "reduces" refers to a negative alteration of at least 10%, 25%, 50%, 75%, or 100%.

The term "reference" refers to a standard or control conditions such as a sample (human cells) or a subject that is a free, or substantially free, of an agent such as Tonabersat.

The term "sensitivity" refers to the percentage of subjects with a particular disease.

The term "SOD1" refers to superoxide dismutase [Cu—Zn] also known as superoxide dismutase 1 or SOD1 is an enzyme that in humans is encoded by the SOD1 gene, located on chromosome 21. SOD1 is one of three human superoxide dismutases.

The term "specificity" refers to the percentage of subjects correctly identified as NOT having a particular disease i.e., normal or healthy subjects.

The term "suppressor of hemichannel permeability" refers to the inhibition of material moved from the cell cytoplasm to the extracellular space through a hemichannel.

The term "subject" refers to any individual or patient to which the method described herein is performed. Generally, the subject is human, although as will be appreciated by those in the art, the subject may be an animal. Thus, other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

The term "range" refers to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

The term "ubiquitin" refers to a small (8.6 kDa) regulatory protein found in most tissues of eukaryotic organisms, i.e. it occurs ubiquitously. Four genes in the human genome code for ubiquitin: UBB, UBC, UBA52 and RPS27A. The addition of ubiquitin to a substrate protein is called ubiquitination (or, less frequently, ubiquitylation or ubiquitinylation). Ubiquitination affects proteins in many ways: it can mark them for degradation via the proteasome, alter their cellular location, affect their activity, and promote or prevent protein interactions.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

As used herein, the terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of diagnosis, staging, screening, or other patient management, including treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

Astrocyte and ALS Pathogenesis.

Recent studies have employed co-cultures of mouse or human embryonic stem cell (ESC)-derived MNs with mSOD1 astrocytes and observed selective destruction of MNs by toxic mutant astrocyte-secreted factors[18,19,20]. The inventor's work, now implicate the astrocyte connexin, Cx43, as a mediator of MN toxicity[21]. Together, these experiments implicate astrocytic influences on MN death and suggest a novel astrocyte/motor neuron interplay in ALS disease progression.

Role of Connexins in Astrocytes.

Astrocytes form a highly coupled intercellular network in the central nervous system (CNS) through gap junctions (GJs)[22]. GJs facilitate intercellular communication with exchange of metabolites[23,24] (glucose, lactate), ions[25,26] (K+, calcium) and second messengers[27,28] (cAMP, IP3, ATP), and more recently, microRNAs[29]. Each GJ is composed of two opposing hemichannels on opposite cell surfaces and each hemichannel is made of 6 connexin subunits arranged around a central pore[30]. While connexins mostly form GJs, they can also exist as "free" hemichannels that open into the extracellular space, especially under pathological conditions[31,32] (FIG. 1).

Cx43 is the predominant connexin in astrocytes and is expressed ubiquitously in a number of tissues. The developmental deletion of Cx43 in all cell types is embryonic lethal due to heart failure; hence conditional $Cx43^{fl/fl}$::GFAP-Cre mice (cKO) have been generated and are viable[33]. This viability is related to the use of GFAP-Cre to KO Cx43 in astrocytes only. Some key roles of Cx43[34] include: homeostatic buffering[35], synchronization of astrocyte networks, metabolic support for neurons[36], regulation of vascular components[37], and modulation of synaptic activity and plasticity, among others.

Cx43 and neurological disease/trauma. Several neurological diseases have reported altered Cx43 expression, gap junction coupling and/or hemichannel activity[32]. In human post-mortem tissues and a mouse model of Alzheimer's disease, Cx43 immunoreactivity is increased, co-localizing with β amyloid (Aβ) plaques[38]. Similar increases in Cx43 expression are reported in models of stroke, retinal and cerebral ischemia, Ceroid Lipofuscinosis (JNCL, lysosomal storage disease). Administration of pan gap junction blockers and Cx43 specific mimetic peptide blocker in these models is found to be neuroprotective and is a potential therapeutic target[39,40,41]. In spinal cord injury (SCI) trauma model, Cx43 is upregulated[42] and SCI in Cx43 cKO mice is milder, exhibiting reduced lesion area, decreased astrogliosis and improved locomotor recovery[43]. Similar observations are reported in traumatic brain injury (TBI) and nerve injury models with Cx43 blockers serving as an effective treatment. The above studies demonstrate a role for astroglial gap junctions and hemichannels in neurological disease/injury. Although a few studies show increased Cx43 in the lumbar spinal cord of SOD1$^{G93A}$ mice[44,45], the role of connexin biology in ALS is largely unexplored.

The methods of the present invention show that the increased expression of Cx43 in SOD1$^{G93A}$ mice is not merely a response to neuronal injury but has a cell autonomous component as well[21]. The inventors have now demonstrated that these increases in Cx43 are functionally and physiologically relevant in an ALS model and that pharmacologically inhibiting Cx43 in SOD1$^{G93A}$ astrocytes can partially protect from MN cell death in vitro.

In accordance with an embodiment, the present invention provides a method for treating or preventing a neurodegenerative disease in a subject in need thereof comprising administering to the subject an effective amount of a suppressor of hemichannel permeability. In some embodiments, the amount of suppressor administered can be modulated where it may or may not also modulate gap junction permeability.

In some embodiments the present invention provides the use of an effective amount of a suppressor of hemichannel permeability so as not to modulate gap junction permeability for treating or preventing a neurodegenerative disease in a subject in need thereof.

The suppressor of hemichannel permeability may be administered to the subject as part of a pharmaceutical composition. In some embodiments, the suppressor of hemichannel permeability is administered in a dose that inhibits hemichannel permeability but not gap junction permeability. Suitable hemichannels that are part of the methods of the present invention may comprise connexin, pannexin, or a combination thereof. In some embodiments, a hemichannel comprises connexin 43 (Cx43).

In some embodiments, the suppressor of hemichannel permeability is a protein or peptide. In certain embodiments, the suppressor is the GAP19 peptide.

The Gap19 peptide is a nonapeptide derived from the cytoplasmic loop of Cx43, and inhibits astroglial Cx43 hemichannels in a dose-dependent manner, and can do so without affecting gap junction channels. This peptide, which not only selectively inhibits hemichannels, but is also specific for Cx43. Gap19 has the amino acid sequence KQIE-IKKFK (SEQ ID NO: 1) and is often fused with TAT peptide for cell penetration as TAT-Gap19 (YGRKKRRQRRR-KQIEIKKFK) (SEQ ID NO: 2).

In some embodiments, the methods of the present invention protect motor neurons of the subject from death.

In some embodiments, the methods of the present invention decrease or minimize the concentration of a motor neuron toxin in a subject.

In some embodiments, the methods of the present invention reduce neuron firing of the subject.

In some embodiments, the methods of the present invention reduce ubiquitin deposition in the motor neurons of the subject.

It will be understood by one of ordinary skill in the art that one or more combinations of these effects can occur.

Tonabersat as an ALS therapeutic.

The inventors' data show that peptide blockers of Cx43 hemichannels provide neuroprotection to MN toxicity (in the context of rodent SOD1$^{G93A}$ astrocyte-induced toxicity) as well as human SOD1$^{44V}$ and sporadic ALS astrocyte-mediated toxicity. However, these peptide blockers have poor CNS penetrability and previous generations of gap junction blockers are non-specific. The inventors' have now identified tonabersat, a small molecule with good BBB penetrability, as a Cx43 HC-specific blocker (at appropriate concentrations)[8], that has the advantage of already being used in humans through studies in patients with migraine.

Therefore, in accordance with a further embodiment, the present invention provides a method for treating ALS comprising administering to a subject in need thereof, an effective amount of tonabersat, or a salt, solvate, derivative or prodrug thereof.

In some embodiments, the present invention provides the use of a suppressor of hemichannel permeability in an effective amount so as not to modulate gap junction permeability in a subject having Amyotrophic Lateral Sclerosis (ALS).

In some embodiments, a suppressor of hemichannel permeability is a compound of Formula (I) and/or Formula (II), a prodrug of Tonabersat, or a combination thereof.

Tonabersat (N-[(3S,4S)-6-acetyl-3-hydroxy-2,2-dimethyl-3,4-dihydro-2H-1-benzopyran-4-yl]-3-chloro-4-fluorobenzamide) and the following structure:

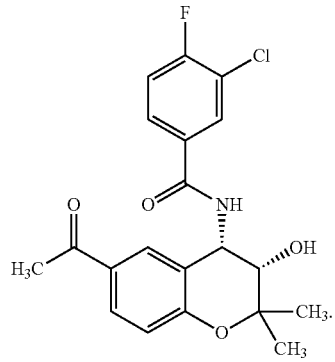

(Formula I)

The compound has an excellent safety profile. The inventors' surprisingly discovered that in the context of ALS, the drug did provide neuroprotection to MN.

In some alternative embodiments, the suppressor of hemichannel permeability is a derivative of tonabersat having the formula:

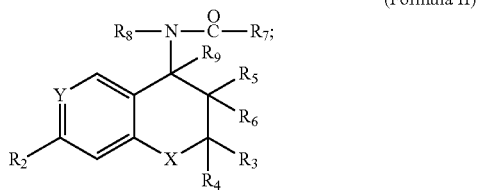

(Formula II)

wherein, Y is C—$R_1$; $R_1$ is acetyl; $R_2$ is hydrogen, $C_{3-8}$ cycloalkyl, $C_{1-6}$ alkyl optionally interrupted by oxygen or substituted by hydroxy, $C_{1-6}$ alkoxy or substituted aminocarbonyl, $C_{1-6}$ alkylcarbonyl, $C_{1-6}$ alkoxy-carbonyl, $C_{1-6}$ alkylcarbonyloxy, $C_{1-6}$ alkoxy, nitro, cyano, halo, trifluoromethyl, or $CF_3$—S; or a group $CF_3$-A-, where A is —$CF_2$, —CO—, —$CH_2$, CH(OH), $SO_2$, SO, $CH_2$—O, or CONH; or a group $CF_2$ H-A'- where A' is oxygen, sulphur, SO, $SO_2$, $CF_2$ or CFH; trifluoromethoxy, $C_{1-6}$ alkylsulphinyl, perfluoro $C_{2-6}$ alkylsulphonyl, $C_{1-6}$ alkylsulphonyl, $C_{1-6}$ alkoxysulphinyl, $C_{1-6}$ alkoxysulphonyl, aryl, heteroaryl, aryl-carbonyl, heteroarylcarbonyl, phosphono, arylcarbonyloxy, heteroarylcarbonyloxy, arylsulphinyl, heteroarylsulphinyl, arylsulphonyl, or heteroarylsulphonyl in which any aromatic moiety is optionally substituted, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mer-capto$C_{2-7}$-alkyl, formyl, or aminosulphinyl, aminosulphonyl or aminocarbonyl, in which any amino moiety is optionally substituted by one or two $C_{1-6}$ alkyl groups, or $C_{1-6}$ alkylsulphinylamino, $C_{1-6}$ alkylsulphonylamino, $C_{1-6}$ alkoxysulphinylamino or $C_{1-6}$ alkoxysulphonylamino, or ethylenyl terminally substituted by $C_{1-6}$ alkylcarbonyl, nitro or cyano, or —C($C_{1-6}$ alkyl)NOH or —C($C_{1-6}$ alkyl)NNH2; or amino optionally substituted by one or two $C_{1-6}$ alkyl or by $C_{2-7}$ alkanoyl; one or $R_3$ and $R_4$ is hydrogen or $C_{1-4}$ alkyl and the other is $C_{1-4}$ alkyl, $CF_3$ or $CH_2X$ is fluoro, chloro, bromo, iodo, $C_{1-4}$ alkoxy, hydrocy, $C_{1-4}$ alkylcarbonyloxy, —S— $C_{1-4}$ alkyl, nitro, amino optionally substituted by one or more $C_{1-4}$ alkyl groups, cyano, or $C_{1-4}$ alkoycarbonyl; or $R_3$ and $R_4$ together are $C_{2-5}$ polymethylene optionally substituted by $C_{1-4}$ alkyl; $R_5$ is $C_{1-6}$ alkylcarbonyloxy, benzoyloxy, $ONO_2$, benzyloxy, phenyloxy or $C_{1-6}$ alkoxy and $R_6$ and $R_9$ are hydrogen or $R_5$ is hydroxy and $R_6$ is hydrogen or $C_{1-2}$ alkyl and $R_9$ is hydrogen; $R_7$ is heteroaryl or phenyl, both of which are optionally substituted one or more times independently with a group or atom selected from chloro, fluoro, bromo, iodo, nitro, amino optionally substituted once or twice by $C_{1-4}$ alkyl, cyano, azido, $C_{1-4}$ alkoxy, trifluoromethoxy and trifluoromethyl; $R_8$ is hydrogen, $C_{1-6}$ alkyl, $OR_{11}$ or $NHCOR_{10}$ wherein $R_{11}$ is hydrogen, $C_{1-6}$ alkyl, formyl, $C_{1-6}$ alkanoyl, aroyl or aryl-$C_{1-6}$ alkyl and $R_{10}$ is hydrogen, $C_{1-6}$ alkyl, $C_{1-6}$ alkoxy, mono or di $C_{1-6}$ alkyl amino, amino, amino-$C_{1-6}$ alkyl, hydroxy-$C_{1-6}$ alkyl, halo-$C_{1-6}$ alkyl, $C_{1-6}$ acyloxy-$C_{1-6}$ alkyl, $C_{1-6}$ alkoxycarbonyl-$C_{1-6}$ -alkyl, aryl or heteroaryl; the $R_8$—N—CO—$R_7$ group being cis to the $R_5$ group; and X is oxygen or $NR_{12}$ where $R_{12}$ is hydrogen or $C_{1-6}$ alkyl.

The term "aliphatic" is an art-recognized term and includes linear, branched, and cyclic alkanes, alkenes or alkynes. In certain embodiments, aliphatic groups in the present invention are linear or branched and have from 1- about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer carbon atoms. Likewise cycloalkyls have from about 3 to about 10 carbon atoms in their ring structure, and alternatively about 5, 6 or 7 carbons in the ring structure.

Moreover, the term "alkyl" (or "lower alkyl") includes both "unsubstituted alkyls" and "substituted alkyls," the latter of which refers to alkyl moieties having substituents replacing hydrogen on one or more carbons of the hydrocarbon backbone. Such substituents may include, for example, a halogen, a hydroxyl, a carbonyl (such as a carboxyl, an alkoxycarbonyl, a formyl or an acyl), a thiocarbonyl (such as a thioester, a thioacetate, or a thioformate), an alkoxyl, a phosphoryl, a phosphonate, a phosphinate, an amino, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls may be further substituted with alkyls, alkenyls, alkoxys, alkylthios, aminoalkyls, carbonyl-substituted alkyls, —$CF_3$, —CN and the like.

The term "aralkyl" is art-recognized, and includes aryl groups (e.g., an aromatic or heteroaromatic group).

The terms "alkenyl" and "alkynyl" are art-recognized, and in an organic molecule, generally includes an atom of any element other than carbon or hydrogen. Illustrative heteroatoms include boron, nitrogen, oxygen, phosphorus, sulfur, and selenium.

The term "aryl" is art-recognized, and includes 5-, 6-, and 7-membered single ring aromatic groups that may include from zero to four heteroatoms, for example, benzene, pyrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydyl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls, and/or heterocyclyls, or rings joined by non-cyclic moieties.

The terms "amine" and "amino" are art-recognized and include both unsubstituted and substituted amines. A primary amine carries two hydrogens, a secondary amine, one hydrogen and another substituent and a tertiary amine, the two hydrogens are substituted. The substituents for one or both of the hydrogens can be, for example, and alkyl, an alkenyl, and aryl, a cycloalkyl, a cycloalkenyl, a heterocycle, a polycycle and so on. If both hydrogens are substituted with carbonyls, the carbonyl framed nitrogen forms an imide.

The term "alkylamine" includes an amine group, as defined above, having a substituted or unsubstituted alkyl attached thereto.

The term "amido" is art-recognized as an amino-substituted carbonyl.

The term "alkylthio" is art-recognized and includes and alkyl group, as defined above, having a sulfur radical attached thereto. In certain embodiments, the "alkylthio" moiety is represented by one of —S-alkyl, —S-alkenyl, —S-alkynyl and so on. Representative alkylthio groups include methylthio, ethylthio and the like.

The term "carbonyl" is art-recognized and includes a C=O structure. Carbonyls are involved in esters; carboxyl groups; formates; thiocarbonyls; thioesters; thiocarboxylic acids; thioformates; ketones; and aldehydes.

The terms "alkoxyl" and "alkoxy" are art-recognized and include an alkyl group, as defined above, having an oxygen radical attached thereto. Representative alkoxyl groups include methoxy, ethoxy, propyloxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl and so on.

The term "sulfonate" is art-recognized and includes a moiety wherein a sulfur atom carries two double bonded oxygens and a single bonded oxygen.

The term "sulfate" is art-recognized and includes a moiety that resembles a sulfonate but includes two single bonded oxygens.

The terms "sulfonamide," "sulfamoyl," "sulfonyl," and "sulfoxido" are art-recognized and each can include a variety of R group substituents as described herein.

The terms phosphoramidite" and "phophonamidite" are art-recognized.

The term "selenoalkyl" is art-recognized and includes an alkyl group having a substituted seleno group attached thereto. Exemplary "selenoethers" which may be substituted on the alkyl are selected from one of —Se-alkyl, —Se-alkenyl, —Se-alkynyl and so on.

Substitutions may be made to alkenyl and alkynyl groups to produce, for example, aminoalkenyls, aminoalkynyls, amidoalkenyls, iminoalkenyls, iminoalkynyls, thioalkenyls, thioalkynyls, carbonyl-substituted alkenyls or alkynyls.

A hydrocarbon is an art recognized term and includes all permissible compounds having at least one hydrogen and one carbon atom. For example, permissible hydrocarbons include acyclic and cyclic, branched and unbranched, carbocyclic and heterocyclic, aromatic and nonaromatic organic compounds that may be substituted or unsubstituted.

Prodrugs of Tonabersat

The following compounds are possible prodrugs of tonabersat which may also be used to treat ALS: (3S,4S)-6-Acetyl-4-[(3-chloro-4-fluorobenzene)amido]-2,2-dimethyl-3,4-dihydro-2H-1-benzopyran-3-yl (2R)-2-amino-3-methylbutanoate; (3S,4S)-6-Acetyl-4-[(3-chloro-4-fluorobenzene)amido]-2,2-dimethyl-3,4-dihydro-2H-1-benzopyran-3-yl (2R)-2-amino-4-methylpentanoate; (3S, 4S)-6-Acetyl-4-[(3-chloro-4-fluorobenzene)amido]-2,2-dimethyl-3,4-dihydro-2H-1-benzopyran-3-yl (2S)-pyrrolidine-2-carboxylate(3S,4S)-6-Acetyl-4-[(3-chloro-4-fluorobenzene)amido]-2,2-dimethyl-3,4-dihydro-2H-1-benzopyran-3-yl 2-amino-2-methylpropanoate; (3S,4S)-6-Acetyl-4-[(3-chloro-4-fluorobenzene)amido]-2,2-dimethyl-3,4-dihydro-2H-1-benzopyran-3-yl3-aminopropanoate; (3S, 4S)-6-Acetyl-4-[(3-chloro-4-fluorobenzene)amido]-2,2-dimethyl-3,4-dihydro-2H-1-benzopyran-3-yl (2S)-2,6-diaminohexanoate; (3S,4S)-6-Acetyl-4-[(3-chloro-4-fluorobenzene)amido]-2,2-dimethyl-3,4-dihydro-2H-1-benzopyran-3-yl (2S)-2-amino-3-carbamoylpropanoate; (3S,4S)-6-Acetyl-4-[(3-chloro-4-fluorobenzene)amido]-2, 2-dimethyl-3,4-dihydro-2H-1-benzopyran-3-yl (2S)-2-amino-4-carbamoylbutanoate; (3S,4S)-6-Acetyl-4-[(3-chloro-4-fluorobenzene)amido]-2,2-dimethyl-3,4-dihydro-2H-1-benzopyran-3-yl (2S)-2-amino-5-carbamimidamidopentanoate; (3S)-4-{[(3S,4S)-6-Acetyl-4-[(3-chloro-4-fluorobenzene)amido]-2,2-dimethyl-3,4-dihydro-2H-1-benzopyran-3-yl]oxy}-3-amino-4-oxobutanoic acid; (4S)-5-{[(3S,4S)-6-Acetyl-4-[(3-chloro-4-fluorobenzene)amido]-2,2-dimethyl-3,4-dihydro-2H-1-benzopyran-3-yl]oxy}-4-amino-5-oxopentanoic acid; ({[(3S,4S)-6-Acetyl-4-[(3-chloro-4-fluorobenzene)amido]-2,2-dimethyl-3,4-dihydro-2H-1-benzopyran-3-yl]oxy}methoxy)(methoxy)phosphinic acid; N-[(3S,4S)-6-Acetyl-3-{[(2S)-2,3-dihydroxypropoxy]methoxy}-2,2-dimethyl-3,4-dihydro-2H-1-benzopyran-4-yl]-3-chloro-4-fluorobenzamide; {[(3S,4S)-6-Acetyl-4-[(4-fluorobenzene)amido]-2,2-di-methyl-3,4-dihydro-2H-1-benzopyran-3-yl]oxy}phosphonic acid; ({[(3S,4S)-6-acetyl-4-[(4-fluorobenzene)amido]-2,2-di-methyl-3,4-dihydro-2H-1-benzopyran-3-yl]oxy}methoxy)phosphonic acid; {[(3S,4S)-6-Acetyl-4-[(3-chlorobenzene)amido]-2,2-di-methyl-3,4-dihydro-2H-1-benzopyran-3-yl]oxy}phosphonic acid; ({[(3S,4S)-6-acetyl-4-[(3-chlorobenzene)amido]-2,2-di-methyl-3,4-dihydro-2H-1-benzopyran-3-yl]oxy}methoxy) phosphonic acid; (3S,4S)-6-Acetyl-4-[(3-chloro-4-fluorobenzene)amido]-2,2-dimethyl-3,4-dihydro-2H-1-benzopyran-3-yl (2S)-2-aminopropanoate; (3 S,4S)-6-Acetyl-4-[(3-chloro-4-fluorobenzene)amido]-2,2-dimethyl-3,4-dihydro-2H-1-benzopyran-3-yl (2S)-2-amino-3-methylbutanoate; (3S,4S)-6-Acetyl-4-[(3-chloro-4-fluorobenzene)amido]-2,2-dimethyl-3,4-dihydro-2H-1-benzopyran-3-yl (2S)-2-(methylamino)propanoate; (3S,4S)-6-Acetyl-4-[(3-chloro-4-fluorobenzene)amido]-2,2-dimethyl-3,4-dihydro-2H-1-benzopyran-3-yl (2S)-2-aminopropanoate; (3S,4S)-6-Acetyl-4-[(3-chloro-4-fluorobenzene)amido]-2,2-dimethyl-3,4-dihydro-2H-1-benzopyran-3-yl (2S)-2-amino-3-methylbutanoate; and (3S, 4S)-6-Acetyl-4-[(3-chloro-4-fluorobenzene)amido]-2,2-dimethyl-3,4-dihydro-2H-1-benzopyran-3-yl (2S)-2-(methylamino)propanoate.

It is well known that ALS astrocytes can induce toxicity to motor neurons and this may be a major factor in ALS pathogenesis. The inventors have now shown that ALS astrocyte-induced MN toxicity is in part mediated by Cx43 hemichannels using a rodent model of ALS. The inventors also now show that a peptide blocker of this hemichannel (Gap 19) can be neuroprotective in this context. The inventors found that using human induced pluripotent stem cells from control and ALS patients to demonstrate that the orally available compound, tonabersat, can protect MNs from ALS astrocyte-induced excitotoxicity as demonstrated in a iPSC-co-culture system. Because tonabersat has previously been used in phase II clinical trials and is well tolerated and safe, the inventors believe that it may be a potential treatment for ALS.

In an embodiment, the present invention provides a method for treating or preventing a neurological disease or disorder, such as ALS, in a subject in need thereof comprising administering to the subject an effective amount of a pharmaceutical composition comprising one or more of tonabersat, a compound of Formula I and/or a compound of formula II, or a salt, solvate, or prodrug of tonabersat, and a pharmaceutically acceptable carrier.

In some embodiments, the invention provides the use of an effective amount of pharmaceutical composition comprising one or more of tonabersat, a compound of Formula I and/or a compound of formula II, or a salt, solvate, or prodrug of tonabersat, and a pharmaceutically acceptable carrier for treating or preventing a neurological disease or disorder, such as ALS, in a subject in need thereof.

Embodiments of the disclosure concern methods and/or compositions for treating and/or preventing a neurological disorder in which modulation of the communication pathway between astrocytes and neurons is directly or indirectly related. In certain embodiments, subjects with a neurological disorder such as amyotrophic lateral sclerosis (ALS) are treated with a modulator of this communications pathway.

In specific embodiments, a subject with ALS is provided a modulator of hemichannels, located on astrocytes. There is no evidence to suggest that CX43 is located on motor neurons. Consequently, it appears motor neurons are substantially free of CX-43 hemichannels.

In specific embodiments, the modulator is a suppressor of hemichannel permeability of materials, for example from inside the astrocyte to its exterior.

In specific embodiments, the hemichannel is a hemichannel composed of Cx43 protein and the suppressor is tonabersat or a prodrug thereof as provided for herein. If a suppressor of hemichannel permeability also suppresses gap junction permeability, then subjects receive a dose of suppressor in a range that suppresses hemichannel permeability, such as Cx43 hemichannel permeability, but not gap junction permeability.

In certain embodiments, the level to which a suppressor of hemichannel permeability may be any level so long as it provides amelioration of at least one symptom of the neurological disorder, including ALS. The level of hemichannel permeability may decrease by at least 2, 3, 4, 5, 10, 25, 50, 100, 1000, or more fold compared to the level of hemichannel permeability in a standard, in at least some cases. An individual may monitor hemichannel permeability and gap junction permeability using standard methods in the art.

In some embodiments, an individual is given an agent for ALS therapy in addition to the one or more suppressors of hemichannel permeability. When combination therapy is employed with one or more suppressors of hemichannel permeability, the additional therapy may be given prior to, at the same time as, and/or subsequent to the suppressor of hemichannel permeability.

In some other embodiments, the one or more suppressors of hemichannel permeability are administered in combination with one or more additional biologically active agents, either together or serially.

An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc. The active agent can be a biological entity, such as a virus or cell, whether naturally occurring or manipulated, such as transformed.

The biologically active agent may vary widely with the intended purpose for the composition. The term active is art-recognized and refers to any moiety that is a biologically, physiologically, or pharmacologically active substance that acts locally or systemically in a subject. Examples of biologically active agents, that may be referred to as "drugs", are described in well-known literature references such as the Merck Index, the Physicians' Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a biologically active agent may be used which are capable of being released the subject composition, for example, into adjacent tissues or fluids upon administration to a subject. In some embodiments, a biologically active agent may be used in cross-linked polymer matrix of this invention, to, for example, promote cartilage formation. In other embodiments, a biologically active agent may be used in cross-linked polymer matrix of this invention, to treat, ameliorate, inhibit, or prevent a disease or symptom, in conjunction with, for example, promoting cartilage formation.

Further examples of biologically active agents include, without limitation, enzymes, receptor antagonists or agonists, hormones, growth factors, autogenous bone marrow, antibiotics, antimicrobial agents, and antibodies. The term "biologically active agent" is also intended to encompass various cell types and genes that can be incorporated into the compositions of the invention. Non-limiting examples of biologically active agents include following: adrenergic blocking agents, anabolic agents, androgenic steroids, antacids, anti-asthmatic agents, anti-allergenic materials, anti-cholesterolemic and anti-lipid agents, anti-cholinergics and sympathomimetics, anti-coagulants, anti-convulsants, anti-diarrheal, anti-emetics, anti-hypertensive agents, anti-infective agents, anti-inflammatory agents such as steroids, non-steroidal anti-inflammatory agents, anti-malarials, anti-manic agents, anti-nauseants, anti-neoplastic agents, anti-obesity agents, anti-parkinsonian agents, anti-pyretic and analgesic agents, anti-spasmodic agents, anti-thrombotic agents, anti-uricemic agents, anti-anginal agents, antihistamines, anti-tussives, appetite suppressants, benzophenanthridine alkaloids, biologicals, cardioactive agents, cerebral dilators, coronary dilators, decongestants, diuretics, diagnostic agents, erythropoietic agents, estrogens, expectorants, gastrointestinal sedatives, agents, hyperglycemic agents, hypnotics, hypoglycemic agents, ion exchange resins, laxatives, mineral supplements, mitotics, mucolytic agents, growth factors, neuromuscular drugs, nutritional substances, peripheral vasodilators, progestational agents, prostaglandins, psychic energizers, psychotropics, sedatives, stimulants, thyroid and anti-thyroid agents, tranquilizers, uterine relaxants, vitamins, antigenic materials, and prodrugs.

Specific examples of useful biologically active agents the above categories include: autonomic agents, such as anticholinergics, antimuscarinic anticholinergics, ergot alkaloids, parasympathomimetics, cholinergic agonist parasympathomimetics, cholinesterase inhibitor parasympathomimetics, sympatholytics, α-blocker sympatholytics, sympatholytics, sympathomimetics, and adrenergic agonist sympathomimetics, for example.

In some embodiments, the biologically active agents can include riluzole, Rilutek, edaravone, Radicava, Tiglutik and Exservan for example.

Pharmaceutical Preparations

Pharmaceutical compositions of the present invention comprise an effective amount of one or more suppressors of hemichannel permeability such as a Cx43 hemichannel, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that comprises at least one suppressor of hemichannel permeability or additional active ingredient will be known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The suppressor of hemichannel permeability may comprise different types of carriers depending on whether it is to be administered in solid, liquid or aerosol form, and whether it need to be sterile for such routes of administration as injection. The present compositions can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The suppressor of hemichannel permeability, such as tonabersat or a prodrug thereof described above, may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

In accordance with some embodiments, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include a suppressor of hemichannel permeability, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the suppressor of hemichannel permeability may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Alimentary Compositions and Formulations

In one embodiment of the present disclosure, the suppressors of hemichannel permeability are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration, the compositions of the present disclosure may alternatively be incorporated with one or more excipients in the form of a mouthwash, dentifrice, buccal tablet, oral spray, or sublingual orally—administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants.

Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Parenteral Compositions and Formulations

In further embodiments, suppressors of hemichannel suppression may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 67,537,514, 6,613,308, 5,466,468, 5,543,158; 5,641,515; and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety).

In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards. Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Miscellaneous Pharmaceutical Compositions and Formulations

In other preferred embodiments of the invention, the active compound suppressor of hemichannels may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts.

Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Kits of the Disclosure

Any of the compositions described herein may be comprised in a kit. In a non-limiting example, a suppressor of hemichannel (for example, Tonabersat or a prodrug thereof as described in FIG. 5) may be comprised in a kit.

The kits may comprise a suitably aliquoted a suppressor of hemichannel permeability and, in some cases, one or more additional agents. The component(s) of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the suppressor of hemichannel permeability and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The suppressor of hemichannel permeability composition(s) may be formulated into an injectable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

The following examples have been included to provide guidance to one of ordinary skill in the art for practicing representative embodiments of the presently disclosed subject matter. In light of the present disclosure and the general level of skill in the art, those of skill can appreciate that the following examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

EXAMPLES

Human iPSC astrocyte culture: The generation, characterization of the human iPSC lines and their differentiation into astrocytes have been previously described by our group[49-51]. Briefly, our 25-30 day spinal cord differentiation protocol relies on extrinsic morphogenetic instructions to pattern neural progenitor cells (NPC) along the rostro-caudal and dorso-ventral axis. For the generation of hiPSC-A, NPC were cultured for up to 90 days in vitro (DIV) with "astrocyte differentiating medium"[58]. The human iPSC-derived astrocyte lines from healthy subjects and both sporadic and familial ALS patients utilized for this study are listed in Table 1. For Western Blot purposes, hiPSC-A from healthy subjects and ALS patients were cultured for 86 DIV and then plated in 6 well plates at a density of 200,000 cells/wells. Astrocytes were allowed to recover and become confluent for 4 days (i.e. 90 DIV) prior to collection of protein samples and immunoblotting.

TABLE 1

Human iPSC-derived astrocyte and MN lines used herein.

| hiPSC astrocyte line | Phenotype |
| --- | --- |
| CS25 | Control |
| CiPS | Control |
| JH082 | Control |
| GO018 | Control |
| JH013 | Slow Sporadic |
| JH036 | Slow Sporadic |
| JH029 | Typical Sporadic |
| JH017 | Typical Sporadic |
| JH058 | Rapid Sporadic |
| JH040 | Rapid Sporadic |
| GO017 | Slow Familial (SOD1$^{D90A}$) |
| GO004 | Slow Familial (SOD1$^{D90A}$) |
| GO 028 | Slow Familial (SOD1$^{D90A}$) |
| GO013 | Rapid Familial (SOD1$^{A4V}$) |
| GO 002 | Rapid Familial (SOD1$^{A4V}$) |
| GO 007 | Rapid Familial (SOD1$^{A4V}$) |
| 39B | Rapid Familial (SOD1$^{A4V}$) |
| 39B2.5 | 39B isogenic corrected line (SOD1$^{+/+}$) |
| hiPSC-MN line | |
| GM01582 | Control |
| CS25 | Control |

Human iPSC-motor neuron culture: Briefly, NPC differentiated with the aforementioned spinal cord patterning protocol were cultured for up to 60 DIV with "neuronal differentiating medium"[58,59]. To prevent astrocyte overproliferation, neuronal cultures were treated once with 0.02 µM cytosine arabinoside (Ara-C) (Millipore Sigma) for 48 h. While the majority of these cells are Tuj1+/ChAT+, consistent with a spinal motor neuronal phenotype, a smaller subset of neurons (Tuj1+/ChAT−) is also present and consists mainly of GABAergic interneurons[58].

Human iPSC-astrocyte and hiPSC-motor neuron co-culture: Human iPSC-A form healthy subjects and ALS patients were cultured for 86 DIV and then plated in 24 well plates on glass cover-slips at a density of 20,000 cells/well. Four days later, hiPSC-MN from control samples, cultured for 60 DIV prior to use, were plated on the top of astrocytes at a density of 50,000 cells/well. This was considered day 1 of co-culture. Co-cultures were maintained in motor neuronal medium enriched with 1% FBS for a total of 14 days before fixing for immunocytochemistry. Co-culture medium was changed every third day with half medium exchange. For pharmacological assays on Cx43 HC, we used GAP19 (Tocris, 53533) at a concentration of 340 μM[21,50] and tonabersat (SB-220453) at concentrations of 1 μM, 10 μM and 100 μM[7,8] (Millipore Sigma, SML1354).

Human iPSC-astrocyte and hiPSC-motor neuron co-culture in a transwell system: Human iPSC-MN from control samples were cultured for 56 DIV and then plated in 12 well plates on glass coverslips at a density of 250,000 cells/well. In parallel cultures, hiPSC-A from healthy subjects and ALS patients were cultured for 86 DIV and then plated in the top inserts of 12 well plates (12 mm diameter, with 0.4 μm pore polyester membrane insert) (Corning, 3460) at a density of 48,000 per insert. Four days later, the inserts with 90 DIV astrocytes were placed on the top of 12-well plates with 60 DIV motor neurons at the bottom. This was considered day 1 of "transwell" co-cultures. Half medium exchanges were performed from both the top and the bottom compartments. Transwell co-culture were otherwise maintained as conventional co-cultures and neurons on glass coverslips were fixed for immunocytochemistry after 14 days.

Multi-electrode array culture and recordings: Multi-electrode array (MEA) plates (MultiChannel Systems, 60MEA200/30iR-Ti-gr,) with 60 electrodes, including 59 active and 1 reference, and a MEA2100 (MultiChannel Systems) platform were used for the recording of neuronal activity in hiPSC-A/-MN co-cultures as we have previously described[50]. Briefly, hiPSC-A from healthy subjects and ALS patients and hiPSC-MN from a single control line were serially co-cultured at densities of 100,000 cells/plate and 500,000 cells/plate, respectively. We analyzed the following electrophysiological parameters: spike rate, burst rate, and percentage of spiking and bursting electrodes (on the overall 59 recording electrodes). The recording of the baseline activity of MEA plates was performed every 3 days over 1-minute period for 2 weeks after initial plating. For pharmacological assays, we performed 5 minutes recordings to capture slower electrophysiological effects of HC blockers36: baseline MEA activity for 1 minute, activity for 1 minute after 100 μl medium exchange with drug vehicle, and activity for 3 minutes after the exchange of 100 μl of medium containing the compound of interest and the drug vehicle. For analysis purposes, we considered only the electrodes with spike rate >0. Spiking and bursting activity is expressed as the mean of individual MEA plates.

Data presentation and statistical analysis: All data were analyzed using GraphPad Prism software (La Jolla, Calif.). Graph bars represent mean±SEM and individual observations are shown as scatter plots. Data were analyzed using Student's t-test, one-way ANOVA or two-way ANOVA, followed by Tukey's test for multiple comparisons as described in figure legends. The statistical significance was set at $p<0.05$ (*$p<0.05$, $p<0.01$, *$p<0.001$). All experiments were performed in at least 3 technical replicates. The number (n) of experimental conditions is indicated in the figure legends.

Example 1

Figures 2A, 2B, 2C, 2D, 2E:
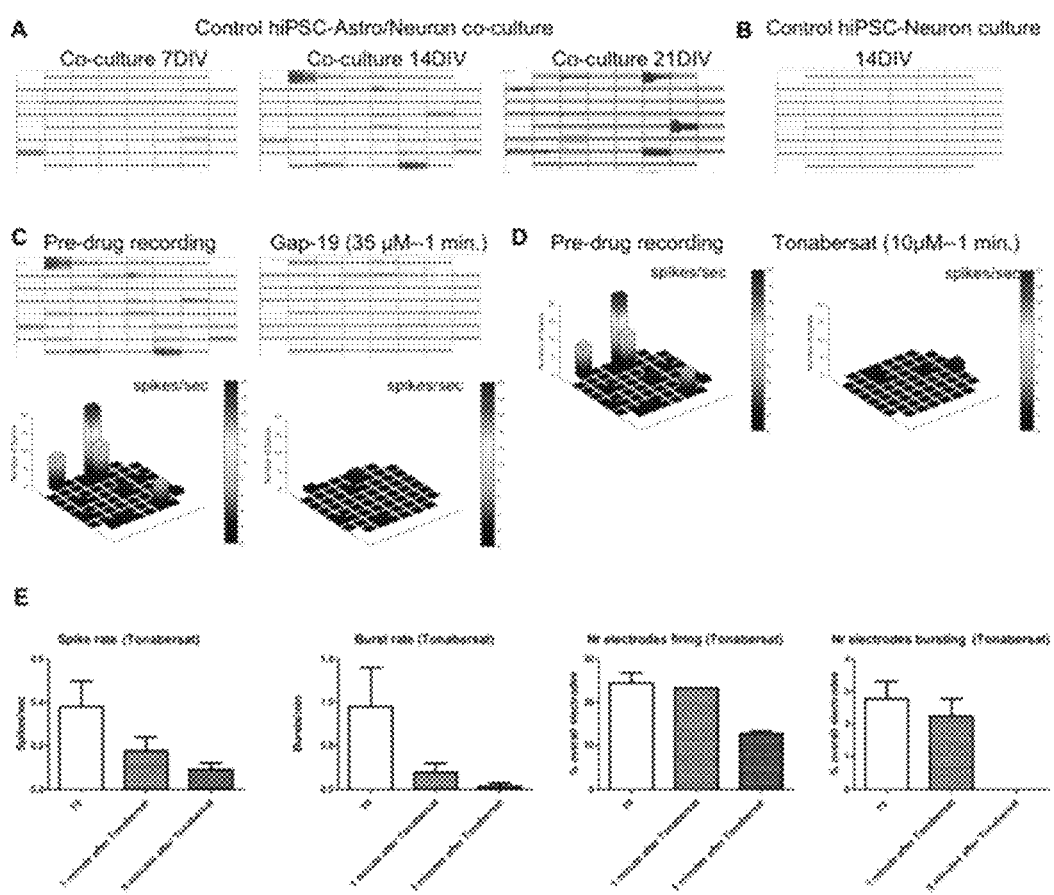
FIGS. 2A-2E show astrocyte influences on neuron firing and effects of CX43 HC blockers.

Multielectrode (MEA) of hiPSC-Astrocyte/Neuron cultures demonstrates astrocyte influences on neuron firing and effects of Cx43 HC blockers. The inventors also wanted to establish the acute effects of hiPSC-derived astrocytes on hIPSC-Neuron spike activity. The inventors utilized a multielectrode array system that allows them to measure neuronal spike activity serially. The inventors first established a time course by which control hiPSC-Astro mature hiPSC-Neurons and show that spike activity increases from 7 DIV to 21 DIV (FIG. 2A). The inventors also verified that in the absence of hiPSC-Astro co-culture, hiPSC-Neurons cultured alone show a delayed maturation in neuronal activity (FIG. 2B). The inventors then utilized the hiPSC-Astro/Neuron co-culture to study how blocking astrocyte Cx43 HC would affect hiPSC-Neuron spike activity. The addition of the Cx43 HC blocker Gap-19 shows reduced neuronal firing 1 minute after application (FIGS. 2C, 2D). Similarly, the application of tonabersat (Cx43-specific HC blocker) reduced hiPSC-Neuron firing 1 and 5 minutes after application. Tonabersat also reduced hiPSC-Neuron spike rate, burst rate, number of electrodes firing and bursting (FIG. 2E).

Example 2

Tonabersat reduces control and ALS IPSC-Astro HC-mediated hiPSC-Neuron firing in a dose-dependent manner.

Figure 3:
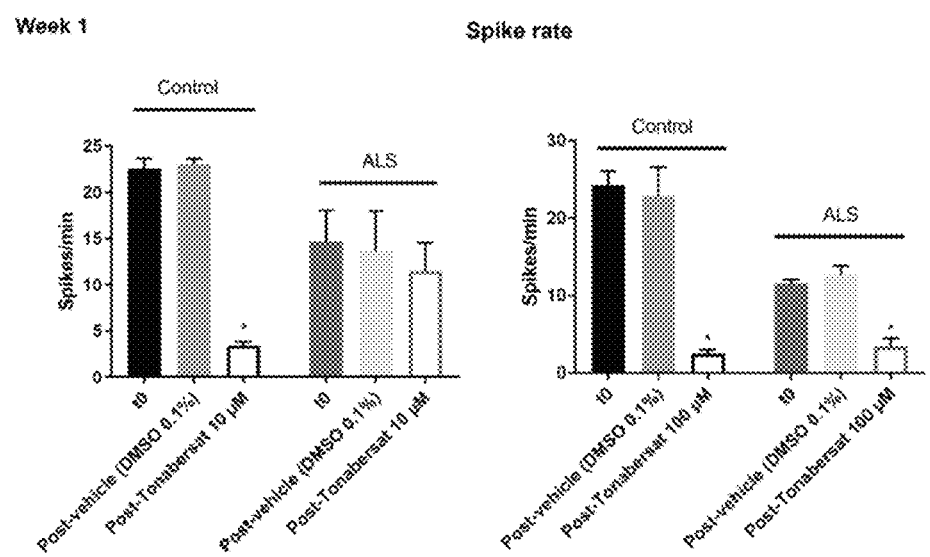
FIG. 3 illustrates Tonabersat reduces control and ALS IPSC-Astro HC-mediated hiPSC-Neuron firing in a dose-dependent manner.
Figures 4A, 4V:
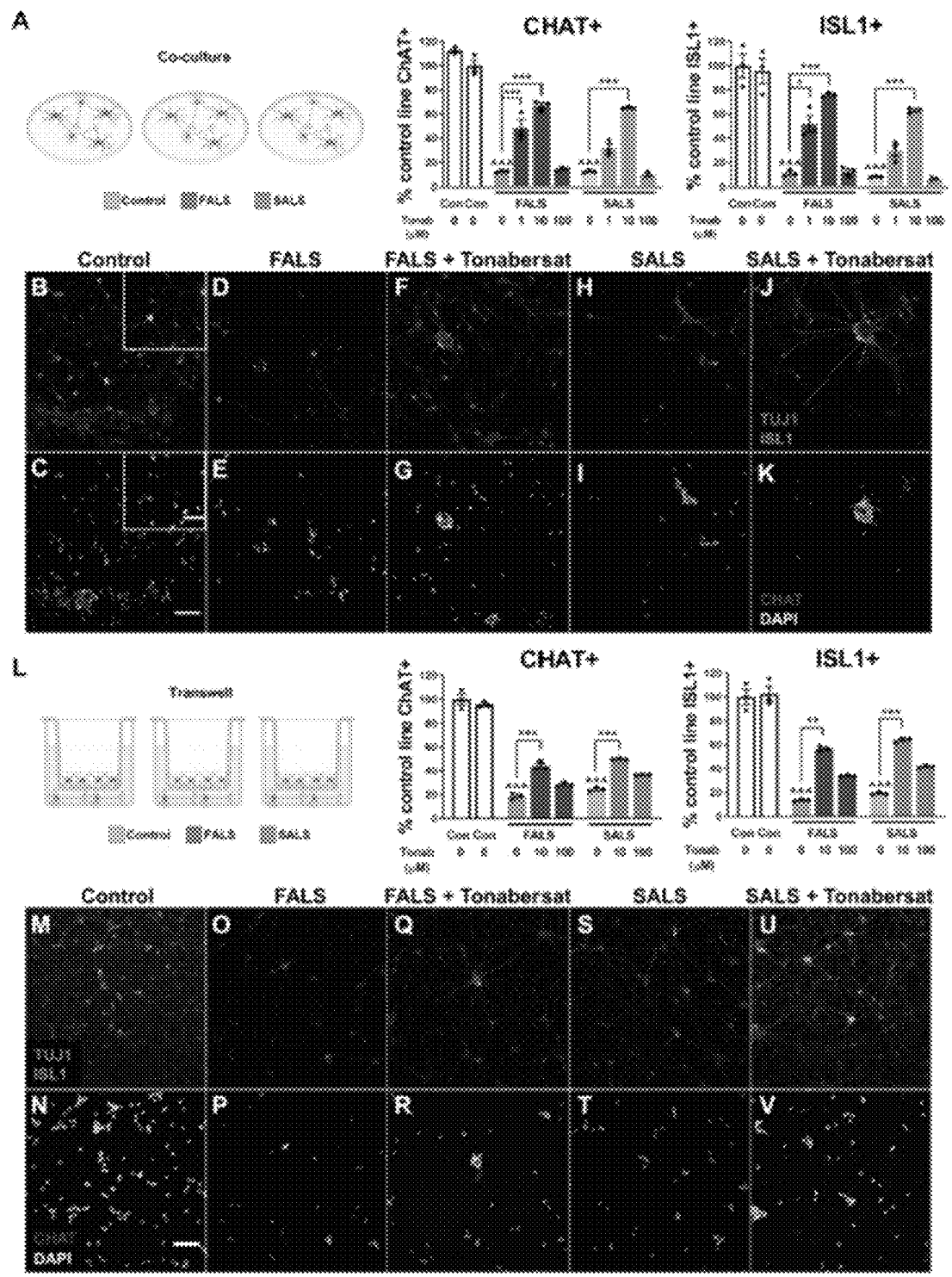
FIGS. 4A-4V: The Cx43 HC blocker tonabersat provides dose-dependent neuroprotection to hiPSC-MN. (4A-K) FALS and SALS hiPSC-A/MN co-culture immunostained for ChAT and Isl-1 shows dose-dependent neuroprotection from tonabersat (1 µM, 10 µM and 100 µM), a small molecule that acts as Cx43 blocker, after a 14 day incubation period. (4L-V) Following transwell co-culture of FALS and SALS hiPSC-A with hiPSC-MN, immunostaining for ChAT$^+$ MN and Isl1$^+$ MN confirms dose-dependent neuroprotection with tonabersat. Significant comparisons (one-way ANOVA) between untreated control and ALS co-cultures are marked with (^), while significant effects of tonabersat on co-cultures containing ALS astrocytes are marked with (*). * or ^p<0.05;  or ^^p<0.01; * or ^^^p<0.001, n=3/condition Scale bar=50 µm, inset scale bar 20 µm. Data are represented as mean±SEM.

Microelectrode array was used for the analysis of the acute effects of tonabersat on hiSPC-Neuron spike activity. Human control and ALS iPSC-Astro were co-cultured with control hiPSC-Neurons for 1 week prior to recording. The application of tonabersat at 10 μM and 100 μM resulted in a reduction of hiPSC-Neuron spike activity 1 minute after application but 100 μM tonabersat is necessary to reduce ALS hiPSC-astrocyte mediated neuron spike activity as measured by MEA (FIG. 3). This phenomenon may reflect our observations that Cx43 and, specifically, Cx43 HC are enriched in ALS human iPSC-astrocytes (not shown).

Example 3

The Cx43 HC blocker tonabersat provides dose-dependent neuroprotection to hiPSC-MN.

The inventors' findings from rodent models and from human ALS samples suggest that Cx43 HC may provide an appropriate target for ALS therapeutics. Tonabersat (SB-220453) was selected for its translational potential in human clinical trials and has been shown[7,8] to specifically block Cx43 HC at low concentrations (1-10 μM).

Figures 5A, 5B, 5C:
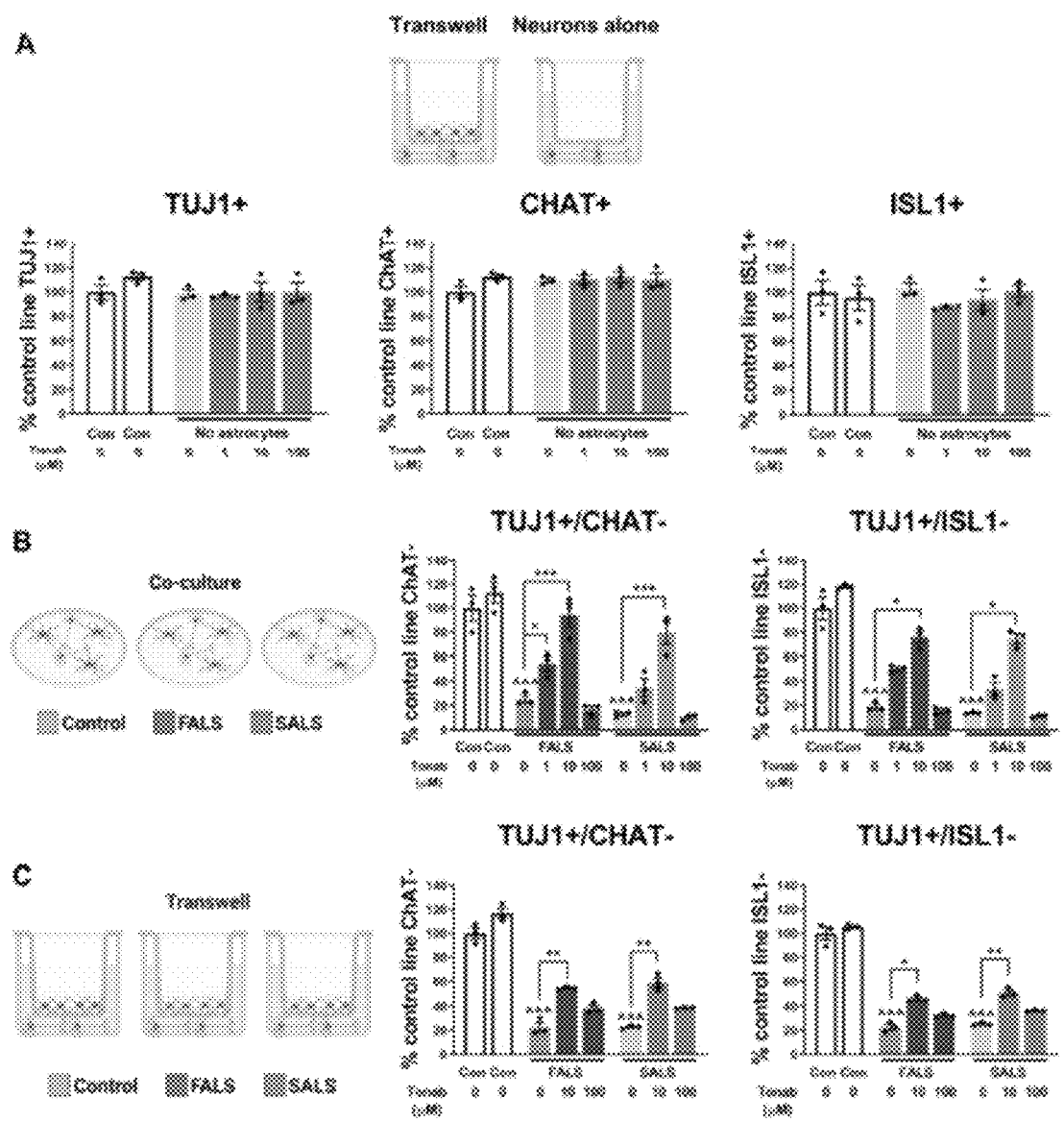
FIGS. 5A-5C: Tonabersat results in neuroprotection of ALS hiPSC-A induced non-motor neuron cell death with no effect on control hiPSC-MN alone or co-cultured with control hiPSC-A. (5A) The application of tonabersat at several concentrations has no effect on ChAT+ and Isl1+ control hiPSC-MN survival, which was independent of culture conditions (alone or in co-culture with control hiPSC-A). (5B) FALS and SALS hiPSC-A induce hiPSC non-motor neuron cell death in a co-culture system as defined by as defined by ChAT$^-$/Tuj1$^+$ and Isl1$^-$/Tuj1$^+$ immunoreactivity that can be rescued with tonabersat. (5C) The transwell culture of FALS and SALS hiPSC-A induce non-motor neuron cell death which can be rescued with tonabersat. One-way ANOVA, * or ^p<0.05;  or ^^p<0.01; * or ^^^p<0.001, n=3. Data are represented as mean±SEM.

To examine the potential of tonabersat in preventing hiPSC-A and Cx43 HC mediated neurotoxicity, we co-cultured control hiPSC-MN with either control hiPSC-A, FALS hiPSC-A, or SALS hiPSC-A. We utilized direct co-culture (FIGS. 4A-K) and transwell (FIGS. 4L-V) paradigms as described above and found that tonabersat protects hiPSC-MN from ALS astrocyte-mediated death in a dose-dependent manner in both systems. At doses of 1 μM and 10 μM, tonabersat blocks Cx43 HC and rescues ChAT+ MNs, including a subpopulation of Isl1+ MN. A higher concentration of 100 μM, tonabersat was not neuroprotective, and likely reflects a long-term effect on reducing gap junction trafficking instead of HC activity, as described previously[8] (FIGS. 4A-K). The neuroprotective effect of tonabersat was also seen in a transwell study (FIGS. 4L-V), suggesting that tonabersat's neuroprotection is HC-mediated and further confirming the importance of Cx43 HC in toxicity. We believe that the neuroprotective effects of tonabersat are specific to Cx43 HC on astrocytes since the application of tonabersat to cultures of hiPSC-MN alone did not have any effect on hiPSC-MN survival (FIG. 5A). Interestingly, we also observed that tonabersat was protective to non-MN populations (ChAT− and Isl1− neurons), similar to the results seen with Gap19 treatment (FIGS. 5B, 5C).

Figures 6A, 6B, 6C, 6D:
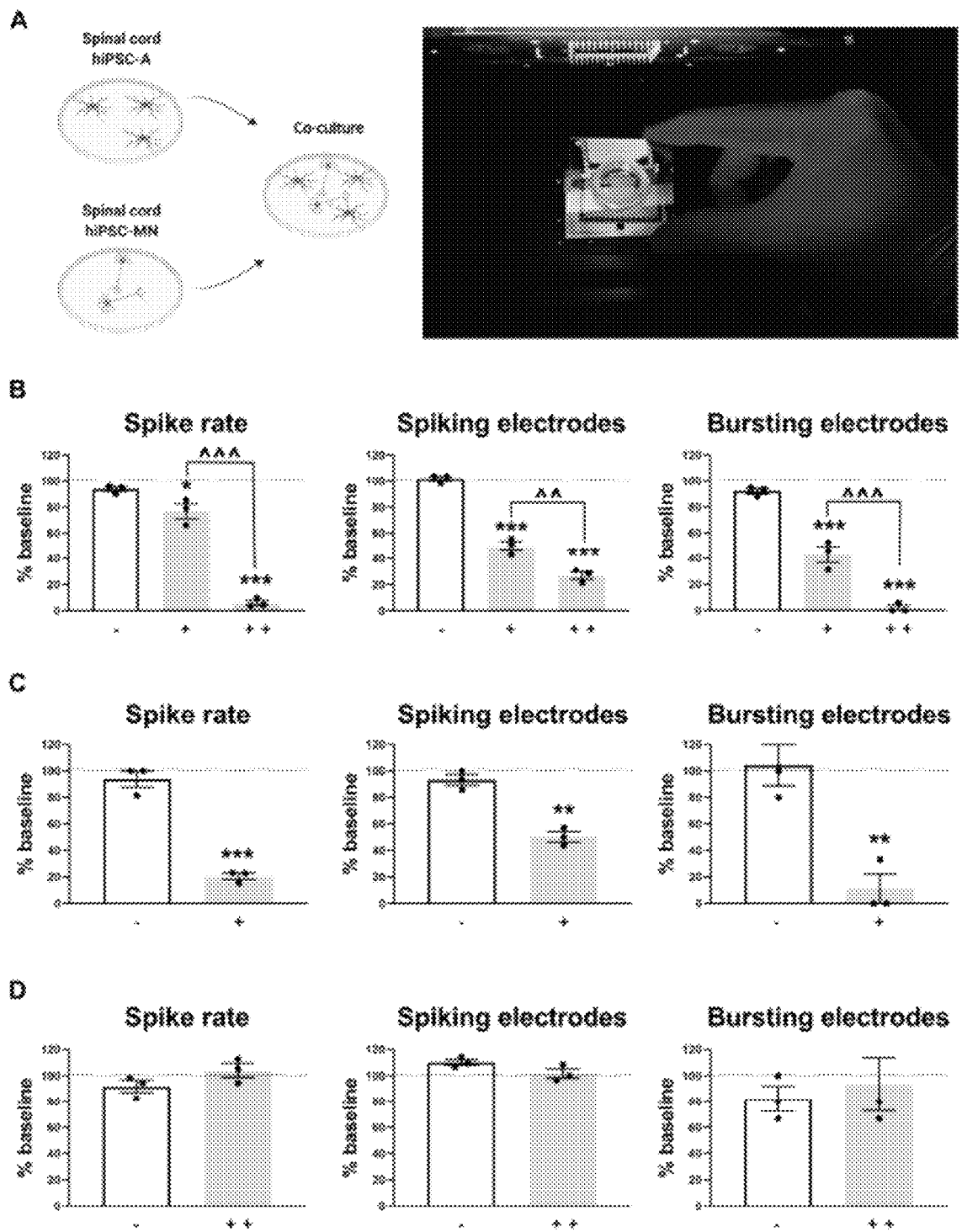
FIGS. 6A-6D. Multielectrode array recordings from hiPSC-A/MN co-cultures. (6A) Control hiPSC-MN and hiPSC-A were plated on multielectrode array (MEA) plates for recording electrophysiological activity (spike rate, percentage of overall electrodes displaying spiking or bursting activity). (6B) MEA electrophysiological activity in control hiPSC-A/-MN co-cultures 5 minutes after the application of vehicle (−), 1 μM (+) and 10 μM (++) tonabersat. (6C) MEA electrophysiological activity in control hiPSC-A/-MN co-cultures 5 minutes after the application of vehicle (−) or 340 μM Gap19 (+). (6D) The addition of 10 μM (++) tonabersat to cultures of control hiPSC alone does not result in an alteration of electrophysiological activity. The electrophysiological parameters are normalized to the baseline activity recorded for 1 minute (dashed line). Data are the mean of n=3 independent experiments per drug. One-way ANOVA, * p<0.05;  p<0.01; * p<0.001. Data are represented as mean±SEM.

In the CNS, tonabersat's actions may translate to an astrocyte-mediated reduction of neuronal excitability[1,54], as suggested by in vivo studies showing tonabersat's inhibitory effects on cortical spreading depression[55,56] and seizures[57,58]. We have previously used[50] multielectrode array (MEA) in a fully human iPSC-based platform to evaluate how astrocytes influence MN electrophysiology (FIG. 6A), and here we employ that system to evaluate the electrophysiological actions of tonabersat in vitro. We first utilized control co-cultures of hiPSC-A/MN on MEA plates to study how the pharmacological blockade of hiPSC-A Cx43 HC would affect hiPSC-MN electrophysiological activity. The addition of tonabersat (FIG. 6B) at a concentration of 10 µM significantly reduced neuronal spiking and bursting activity within 5 minutes of application. The effect was dose-dependent, as a lower concentration of tonabersat (i.e. 1 µM) was less effective (FIG. 6B). These actions parallel those of Cx43 HC-specific blocker Gap19 (FIG. 6C), confirming our previous observations that Cx43 HC influences neuronal firing[50]. To ensure that these effects were astrocyte-mediated, we tested tonabersat on hiPSC-MN alone in culture and did not observe any change in neuronal electrophysiological activity (FIG. 6D).

Figures 7A, 7B, 7C:
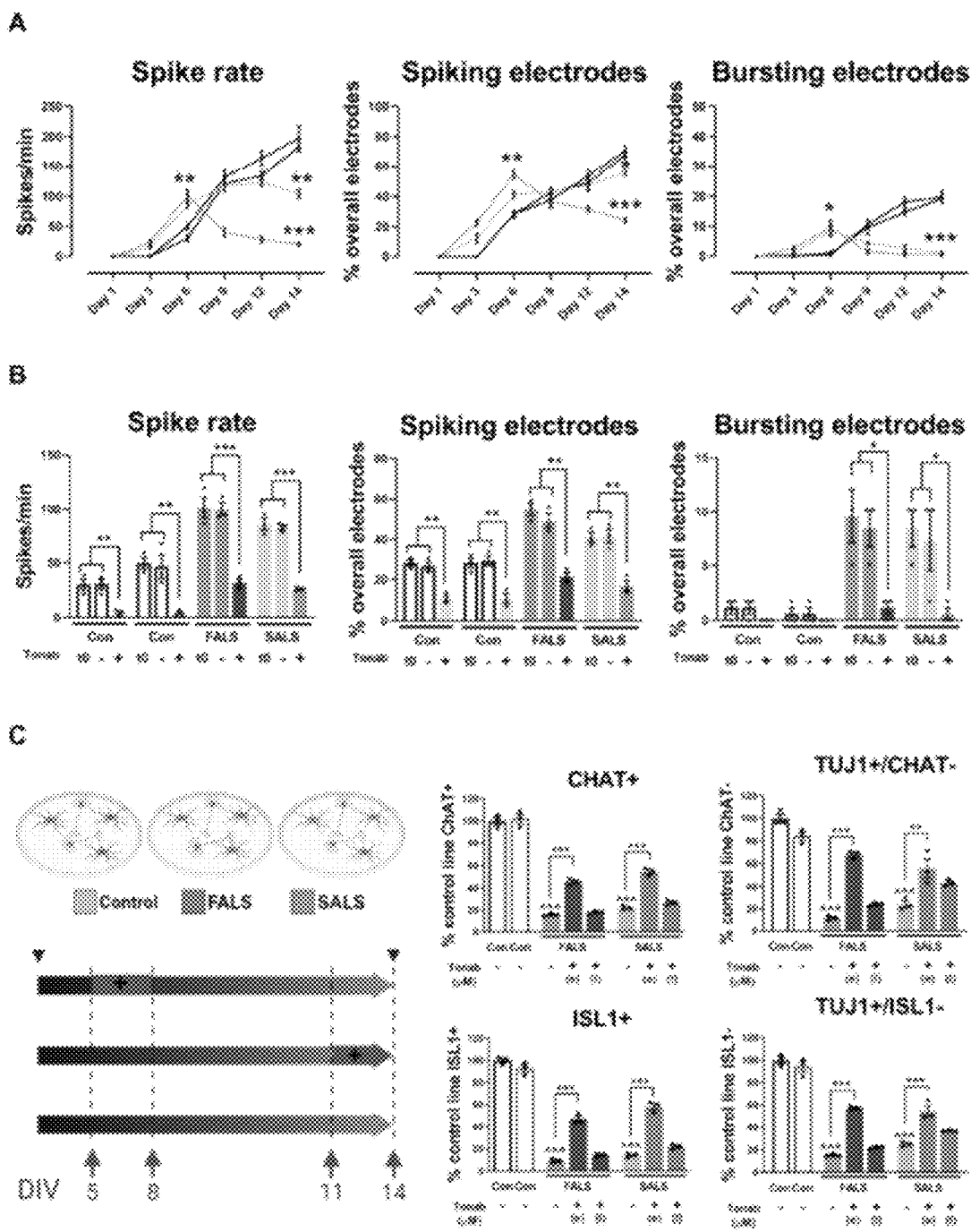
FIGS. 7A-7C. Multielectrode array recordings (MEA) from hiPSC-Astro/MN cultures demonstrate that tonabersat Cx43 HC-mediated effects on hiPSC-MN electrophysiology correlates with its neuroprotective actions. (7A) Multielectrode array recording of neuronal activity (spike rate, percentage of overall MEA electrodes displaying spiking or bursting activity) over-time from co-cultures between control hiPSC-MN and control or ALS hiPSC-A. The presence of SALS and FALS astrocytes when compared to control astrocytes determines early increases in spiking and bursting activity followed, at later time points, by reduced electrophysiological activity. Most significant time-point comparisons (i.e. day 6 and day 14 of co-culture) between control and ALS conditions are marked with (*). Data are mean±SEM (mean of n=3 MEA plates per condition, one-way ANOVA). (7B) MEA activity within 5 minutes after the application of 10 μM tonabersat (+) on co-cultures with control or ALS hiPSC-A compared to baseline (t0) and vehicle (−). MEA baseline activity is day 6 time point shown in FIG. 7A. Tonabersat results in significant inhibition (*) of neuronal spiking and bursting activity. (7C) The effects of 10 μM tonabersat (+) on hiPSC-neurons survival in control and ALS co-cultures was tested as outlined in FIG. 4, but for a shorter time course of 3 days, either early (DIV 5 to 8, or "e") or late (DIV 11-14 or "1") during co-culture. Significant neuroprotection was appreciated after early but not late exposure to tonabersat, and was evident for both motor neuronal (ChAT+ and ISL1+ cells) and non-motor neuronal cell types (TUJ1+/ChAT−, TUJ1+/ISL1+). Significant comparisons (one-way ANOVA) between untreated control and ALS co-cultures are marked with (^), while significant effects of tonabersat on co-cultures containing ALS astrocytes are marked with (*). * or ^p<0.05;  or ^^p<0.01; * or ^^^p<0.001, n=3/condition. Data are represented as mean±SEM.

We then evaluated these electrophysiological findings in the context of ALS (FIG. 7). Human control and ALS hiPSC-A were co-cultured with control hiPSC-MN and then recorded serially for 2 weeks. We observed a transient increase in neuronal spiking and bursting activity in the co-cultures with SALS and FALS hiPSC-A when compared to control co-cultures (FIG. 7A), which occurred early during the 2-week recording period (most significantly at DIV 6 of co-culture), followed by a depression of electrophysiological activity (particularly at DIV 14 of co-culture). This transient ALS astrocyte-mediated hyperexcitability was significantly reduced by the acute treatment with tonabersat (FIG. 7B), to levels of spiking and bursting activity not significantly different from those of the untreated control co-cultures.

We then evaluated whether this ALS astrocyte-mediated neuronal hyperexcitability correlated temporally with our previous findings on ALS astrocyte and Cx43 HC mediated neurotoxicity. To address this, we used the co-culture paradigm with ALS and control hiPSC-A/MN co-cultures but with an abbreviated course of treatment with tonabersat (FIG. 7C). Interestingly, we observed neuroprotection of control hiPSC-MN in co-culture with ALS hiPSC-A only when 10 µM tonabersat was applied at an early-time point (i.e. from day 5 to day 8 of co-culture), which corresponded to the period of neuronal hyperexcitability as recorded by MEA. This protection did not occur at a later time-point (from day 11 to day 14 of co-culture), when MEA demonstrated neuronal hypoactivity in co-cultures with ALS hiPSC-A. These effects were not limited to MNs, as we observed similar neuroprotection for ChAT⁻ neurons as well (FIG. 7C).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

1 Chan, W. N. et al. Identification of (−)-cis-6-acetyl-4S-(3-chloro-4-fluoro-benzoylamino)-3,4-dihydro-2,2-dimethyl-2H-benzo[b]pyran-3S-ol as a potential antimigraine agent. *Bioorg Med Chem Lett* 9, 285-290 (1999).
2 Read, S. J., Smith, M. I., Hunter, A. J., Upton, N. & Parsons, A. A. SB-220453, a potential novel antimigraine agent, inhibits nitric oxide release following induction of cortical spreading depression in the anaesthetized cat. *Cephalalgia* 20, 92-99, doi:10.1046/j.1468-2982.2000.00022.x (2000).
3 Durham, P. L. & Garrett, F. G. Neurological mechanisms of migraine: potential of the gap junction modulator tonabersat in prevention of migraine. *Cephalalgia* 29 Suppl 2, 1-6, doi:10.1111/j.1468-2982.2009.01976.x (2009).
4 Hauge, A. W., Asghar, M. S., Schytz, H. W., Christensen, K. & Olesen, J. Effects of tonabersat on migraine with aura: a randomised, double-blind, placebo-controlled crossover study. *Lancet neurology* 8, 718-723, doi:10.1016/S1474-4422(09)70135-8 (2009).
5 Goadsby, P. J. et al. Randomized, double-blind, placebo-controlled, proof-of-concept study of the cortical spreading depression inhibiting agent tonabersat in migraine prophylaxis. *Cephalalgia* 29, 742-750, doi:10.1111/j.1468-2982.2008.01804.x (2009).
6 Damodaram, S., Thalakoti, S., Freeman, S. E., Garrett, F. G. & Durham, P. L. Tonabersat inhibits trigeminal ganglion neuronal-satellite glial cell signaling. *Headache* 49, 5-20, doi:10.1111/j.1526-4610.2008.01262.x (2009).
7 Chen, Q. et al. Carcinoma-astrocyte gap junctions promote brain metastasis by cGAMP transfer. *Nature* 533, 493-498, doi:10.1038/nature18268 (2016).
8 Kim, Y. et al. Tonabersat Prevents Inflammatory Damage in the Central Nervous System by Blocking Connexin43 Hemichannels. *Neurotherapeutics: the journal of the American Society for Experimental NeuroTherapeutics* 14, 1148-1165, doi:10.1007/s13311-017-0536-9 (2017).

9 Clement, A. M. et al. Wild-type nonneuronal cells extend survival of SOD1 mutant motor neurons in ALS mice. *Science* 302, 113-117, doi:10.1126/science.1086071 302/5642/113 [pii] (2003).
10 Bruijn, L. I. et al. ALS-linked SOD1 mutant G85R mediates damage to astrocytes and promotes rapidly progressive disease with SOD1-containing inclusions. *Neuron* 18, 327-338 (1997).
11 Schiffer, D., Cordera, S., Giordana, M. T., Attanasio, A. & Pezzulo, T. Synaptic vesicle proteins, synaptophysin and chromogranin A in amyotrophic lateral sclerosis. *J Neurol Sci* 129 Suppl, 68-74, doi:0022510X9500068D [pii] (1995).
12 Hall, E. D., Oostveen, J. A. & Gurney, M. E. Relationship of microglial and astrocytic activation to disease onset and progression in a transgenic model of familial ALS. *Glia* 23, 249-256 (1998).
13 Howland, D. S. et al. Focal loss of the glutamate transporter EAAT2 in a transgenic rat model of SOD1 mutant-mediated amyotrophic lateral sclerosis (ALS). *Proceedings of the National Academy of Sciences of the United States of America* 99, 1604-1609, doi:10.1073/pnas.032539299 (2002).
14 Rothstein, J. D., Van Kammen, M., Levey, A. I., Martin, L. J. & Kuncl, R. W. Selective loss of glial glutamate transporter GLT-1 in amyotrophic lateral sclerosis. *Ann Neurol* 38, 73-84, doi:10.1002/ana.410380114 (1995).
15 Yamanaka, K. et al. Astrocytes as determinants of disease progression in inherited amyotrophic lateral sclerosis. *Nature neuroscience* 11, 251-253, doi:10.1038/nn2047 (2008).
16 Endo, F. & Yamanaka, K. Astrocytic TGF-beta1: detrimental factor in ALS. *Oncotarget* 6, 15728-15729, doi: 10.18632/oncotarget.4786 (2015).
17 Lepore, A. C. et al. Focal transplantation-based astrocyte replacement is neuroprotective in a model of motor neuron disease. *Nat. Neurosci.* 11, 1294-1301 (2008).
18 Marchetto, M. C. et al. Non-cell-autonomous effect of human SOD1 G37R astrocytes on motor neurons derived from human embryonic stem cells. *Cell stem cell* 3, 649-657 (2008).
19 Di Giorgio, F. P., Carrasco, M. A., Siao, M. C., Maniatis, T. & Eggan, K. Non-cell autonomous effect of glia on motor neurons in an embryonic stem cell-based ALS model. *Nature neuroscience* 10, 608-614, doi:10.1038/nn1885 (2007).
20 Nagai, M. et al. Astrocytes expressing ALS-linked mutated SOD1 release factors selectively toxic to motor neurons. *Nat Neurosci* 10, 615-622, doi:nn1876 [pii] 10.1038/nn1876 (2007).
21 Almad, A. A. et al. Connexin 43 in astrocytes contributes to motor neuron toxicity in amyotrophic lateral sclerosis. *Glia* 64, 1154-1169, doi:10.1002/glia.22989 (2016).
22 Konietzko, U. & Muller, C. M. Astrocytic dye coupling in rat hippocampus: topography, developmental onset, and modulation by protein kinase C. *Hippocampus* 4, 297-306, doi:10.1002/hipo.450040313 (1994).
23 Tabernero, A., Giaume, C. & Medina, J. M. Endothelin-1 regulates glucose utilization in cultured astrocytes by controlling intercellular communication through gap junctions. *Glia* 16, 187-195, doi:10.1002/(SICI)1098-1136(199603)16:3<187::AID-GLIA1>3.0.CO; 2-# [pii] 10.1002/(SICI)1098-1136(199603)16:3< 187::AID-GLIA1> 3.0.CO;2-# (1996).
24 Goldberg, G. S., Lampe, P. D. & Nicholson, B. J. Selective transfer of endogenous metabolites through gap junctions composed of different connexins. *Nat Cell Biol* 1, 457-459, doi:10.1038/15693 (1999).
25 Qu, Y. & Dahl, G. Function of the voltage gate of gap junction channels: selective exclusion of molecules. *Proc Natl Acad Sci USA* 99, 697-702, doi:10.1073/pnas.022324499 99/2/697 [pii] (2002).
26 Christ, G. J., Moreno, A. P., Melman, A. & Spray, D. C. Gap junction-mediated intercellular diffusion of Ca2+ in cultured human corporal smooth muscle cells. *Am J Physiol* 263, $C_{373-383}$ (1992).
27 Lawrence, T. S., Beers, W. H. & Gilula, N. B. Transmission of hormonal stimulation by cell-to-cell communication. *Nature* 272, 501-506 (1978).
28 Saez, J. C., Connor, J. A., Spray, D. C. & Bennett, M. V. Hepatocyte gap junctions are permeable to the second messenger, inositol 1,4,5-trisphosphate, and to calcium ions. *Proc Natl Acad Sci USA* 86, 2708-2712 (1989).
29 Zong, L., Zhu, Y., Liang, R. & Zhao, H. B. Gap junction mediated miRNA intercellular transfer and gene regulation: A novel mechanism for intercellular genetic communication. *Scientific reports* 6, 19884, doi:10.1038/srep19884 (2016).
30 Musil, L. S. & Goodenough, D. A. Multisubunit assembly of an integral plasma membrane channel protein, gap junction connexin43, occurs after exit from the ER. *Cell* 74, 1065-1077, doi:0092-8674(93)90728-9 [pii] (1993).
31 Spray, D. C., Ye, Z. C. & Ransom, B. R. Functional connexin "hemichannels": a critical appraisal. *Glia* 54, 758-773, doi:10.1002/glia.20429 (2006).
32 Orellana, J. A. et al. Modulation of brain hemichannels and gap junction channels by pro-inflammatory agents and their possible role in neurodegeneration. *Antioxid Redox Signal* 11, 369-399, doi:10.1089/ars.2008.2130 (2009).
33 Theis, M. et al. General and conditional replacement of connexin43-coding DNA by a lacZ reporter gene for cell-autonomous analysis of expression. *Cell Commun Adhes* 8, 383-386 (2001).
34 Giaume, C. & Theis, M. Pharmacological and genetic approaches to study connexin-mediated channels in glial cells of the central nervous system. *Brain Res Rev* 63, 160-176, doi:S0165-0173(09)00125-8 [pii]10.1016/j.brainresrev.2009.11.005 (2010).
35 Wallraff, A. et al. The impact of astrocytic gap junctional coupling on potassium buffering in the hippocampus. *J Neurosci* 26, 5438-5447, doi:26/20/5438 [pii] 10.1523/JNEUROSCI.0037-06.2006 (2006).
36 Rouach, N., Koulakoff, A., Abudara, V., Willecke, K. & Giaume, C. Astroglial metabolic networks sustain hippocampal synaptic transmission. *Science* 322, 1551-1555, doi:322/5907/1551 [pii]10.1126/science.1164022 (2008).
37 Mulligan, S. J. & MacVicar, B. A. Calcium transients in astrocyte endfeet cause cerebrovascular constrictions. *Nature* 431, 195-199, doi:10.1038/nature02827 nature02827 [pii] (2004).
38 Mei, X., Ezan, P., Giaume, C. & Koulakoff, A. Astroglial connexin immunoreactivity is specifically altered at beta-amyloid plaques in beta-amyloid precursor protein/presenilin1 mice. *Neuroscience* 171, 92-105, doi:S0306-4522(10)01065-1 [pii] 10.1016/j.neuroscience.2010.08.001 (2010).
39 Kerr, N. M. et al. High pressure-induced retinal ischaemia reperfusion causes upregulation of gap junction protein connexin43 prior to retinal ganglion cell loss. *Exp Neurol* 234, 144-152, doi:S0014-4886(11)00479-1 [pii] 10.1016/j.expneurol.2011.12.027 (2012).

40 Chew, S. S., Johnson, C. S., Green, C. R. & Danesh-Meyer, H. V. Role of connexin43 in central nervous system injury. *Exp Neurol* 225, 250-261, doi:S0014-4886(10)00252-9 [pii]10.1016/j.expneurol.2010.07.014 (2010).

41 Davidson, J. O. et al. Connexin hemichannel blockade improves outcomes in a model of fetal ischemia. *Ann Neurol* 71, 121-132, doi:10.1002/ana.22654 (2012).

42 Lee, I. H., Lindqvist, E., Kiehn, O., Widenfalk, J. & Olson, L. Glial and neuronal connexin expression patterns in the rat spinal cord during development and following injury. *J Comp Neurol* 489, 1-10, doi:10.1002/cne.20567 (2005).

43 Huang, C. et al. Critical role of connexin 43 in secondary expansion of traumatic spinal cord injury. *The Journal of neuroscience: the official journal of the Society for Neuroscience* 32, 3333-3338, doi:10.1523/JNEUROSCI.1216-11.2012 (2012).

44 Diaz-Amarilla, P. et al. Phenotypically aberrant astrocytes that promote motoneuron damage in a model of inherited amyotrophic lateral sclerosis. *Proc Natl Acad Sci U S A* 108, 18126-18131, doi:1110689108 [pii] 10.1073/pnas.1110689108 (2011).

45 Keller, A. F., Gravel, M. & Kriz, J. Treatment with minocycline after disease onset alters astrocyte reactivity and increases microgliosis in SOD1 mutant mice. *Exp Neurol* 228, 69-79, doi:S0014-4886(10)00432-2 [pii] 10.1016/j.expneurol.2010.12.010 (2011).

46 Chio, A. et al. The Role of APOE in the Occurrence of Frontotemporal Dementia in Amyotrophic Lateral Sclerosis. *JAMA Neurol* 73, 425-430, doi:10.1001/jamaneurol.2015.4773 (2016).

47 Kato, S. et al. Absence of SOD1 gene abnormalities in familial amyotrophic lateral sclerosis with posterior column involvement without Lewy-body-like hyaline inclusions. *Acta Neuropathol* 92, 528-533 (1996).

48 Guo, Y. S. et al. Sensory involvement in the SOD1-G93A mouse model of amyotrophic lateral sclerosis. *Exp Mol Med* 41, 140-150, doi:10.3858/emm.2009.41.3.017 (2009).

49 Haidet-Phillips, A. M. et al. Astrocytes from familial and sporadic ALS patients are toxic to Motor neurons. *Nat Biotechnol* 29, 824-828, doi:10.1038/nbt.1957 (2011).

50 Taga, A. et al. Role of Human-Induced Pluripotent Stem Cell-Derived Spinal Cord Astrocytes in the Functional Maturation of Motor Neurons in a Multielectrode Array System. *Stem Cells Transl Med*, doi:10.1002/sctm.19-0147 (2019).

51 Roybon, L. et al. Human stem cell-derived spinal cord astrocytes with defined mature or reactive phenotypes. *Cell reports* 4, 1035-1048, doi:10.1016/j.celrep.2013.06.021 (2013).

52 Boulting, G. L. et al. A functionally characterized test set of human induced pluripotent stem cells. *Nat Biotechnol* 29, 279-286, doi:10.1038/nbt.1783 (2011).

53 Herdon H J, Jerman J C, Stean T O, Middlemiss D N, Chan W N, Vong A K, et al. Characterization of the binding of [31-1]-SB-204269, a radiolabelled form of the new anticonvulsant SB-204269, to a novel binding site in rat brain membranes. *Br J Pharmacol.* 1997; 121(8): 1687-91.

54 Tvedskov J F, Iversen H K, and Olesen J. A double-blind study of SB-220453 (Tonerbasat) in the glyceryltrinitrate (GTN) model of migraine. *Cephalalgia.* 2004; 24(10): 875-82.

55 Bradley D P, Smith M I, Netsiri C, Smith J M, Bockhorst K H, Hall L D, et al. Diffusion-weighted MRI used to detect in vivo modulation of cortical spreading depression: comparison of sumatriptan and tonabersat. *Exp Neurol.* 2001; 172(2):342-53.

56 Upton N, Blackburn T P, Campbell Calif., Cooper D, Evans M L, Herdon H J, et al. Profile of SB-204269, a mechanistically novel anticonvulsant drug, in rat models of focal and generalized epileptic seizures. *Br J Pharmacol.* 1997; 121(8):1679-86.

57 Upton N, and Thompson M. Benzo[b]pyranols and related novel antiepileptic agents. *Prog Med Chem.* 2000; 37:177-200.

58 Rash J E, Yasumura T, Davidson K G, Furman C S, Dudek F E, and Nagy J I. Identification of cells expressing Cx43, Cx30, Cx26, Cx32 and Cx36 in gap junctions of rat brain and spinal cord. *Cell Commun Adhes.* 2001; 8(4-6):315-20.

59 Yi C, Mei X, Ezan P, Mato S, Matias I, Giaume C, et al. Astroglial connexin43 contributes to neuronal suffering in a mouse model of Alzheimer's disease. *Cell Death Differ.* 2016; 23(10):1691-701.

The invention claimed is:

1. A method for minimizing a concentration of a motor neuron toxin in a subject having a neurodegenerative disease comprising administering to the subject a suppressor of hemichannel permeability at a dose that inhibits hemichannel permeability but not gap junction permeability, wherein the suppressor of hemichannel permeability is tonabersat, or a salt, solvate or prodrug thereof.

2. The method of claim 1 wherein the neurodegenerative disease is amyotrophic Lateral Sclerosis (ALS).

3. The method of claim 1, wherein a pharmaceutical composition of the suppressor of hemichannel permeability is administered to the subject.

4. The method of claim 1, wherein the hemichannel is connexin or pannexin.

5. The method of claim 1, wherein the hemichannel is connexin 43 (Cx43).

6. The method of claim 1, further comprising the step of protecting motor neurons of the subject from death.

7. The method of claim 1, further comprising the step of reducing neuron firing of the subject.

8. The method of claim 1, further comprising the step of reducing ubiquitin deposition in the motor neurons of the subject.

9. A method for treatment of Amyotrophic Lateral Sclerosis (ALS) in a subject in need thereof comprising administering to the subject a suppressor of hemichannel permeability at a dose that inhibits hemichannel permeability but not gap junction permeability, wherein the suppressor of hemichannel permeability is tonabersat, or a salt, solvate or prodrug thereof.

10. The method of claim 9, wherein a pharmaceutical composition of the suppressor of hemichannel permeability is administered to the subject.

11. The method of claim 9, wherein the hemichannel is connexin or pannexin.

12. The method of claim 9, wherein the hemichannel is connexin 43 (Cx43).

13. The method of claim 9, further comprising the step of protecting motor neurons of the subject from death.

14. The method of claim 9, further comprising the step of minimizing a concentration of a motor neuron toxin in a subject.

15. The method of claim 9, further comprising the step of reducing neuron firing of the subject.

16. The method of claim 9, further comprising the step of reducing ubiquitin deposition in the motor neurons of the subject.

17. A method for treatment of Amyotrophic Lateral Sclerosis (ALS) in a subject in need thereof comprising administering to the subject a suppressor of connexin and/or pannexin permeability at a dose that inhibits hemichannel permeability but not gap junction permeability, wherein the suppressor of connexin and/or pannexin permeability is tonabersat or a salt or solvate thereof.

18. The method of claim 17, wherein the neurodegenerative disease is amyotrophic Lateral Sclerosis (ALS).

19. The method of claim 17, wherein a pharmaceutical composition of the suppressor of connexin and/or pannexin permeability is administered to the subject.

20. The method of claim 17, wherein the connexin is connexin 43 (Cx43).

21. The method of claim 17, further comprising the step of protecting motor neurons of the subject from death.

22. The method of claim 17, further comprising the step of minimizing a concentration of a motor neuron toxin in a subject.

23. The method of claim 17, further comprising the step of reducing neuron firing of the subject.

24. The method of claim 17, further comprising the step of reducing ubiquitin deposition in the motor neurons of the subject.

25. A method for treatment of Amyotrophic Lateral Sclerosis (ALS) in a subject in need thereof comprising administering to the subject an effective amount of tonabersat, or a salt, solvate or prodrug thereof,
wherein the tonabersat, or a salt, solvate or prodrug thereof is administered at a dose that inhibits hemichannel permeability but not gap junction permeability.

26. The method of claim 25, wherein tonabersat has the formula of Formula (I):

(Formula I)

27. The method of claim 25, further comprising administering to the subject one or more additional biologically active agents.

\* \* \* \* \*

UNITED STATES PATENT AND TRADEMARK OFFICE
CERTIFICATE OF CORRECTION

| | |
|---|---|
| PATENT NO. | : 11,717,506 B2 |
| APPLICATION NO. | : 16/868764 |
| DATED | : August 8, 2023 |
| INVENTOR(S) | : Nicholas J. Maragakis |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 336 days.

The filing date at item (22), "July 1, 2020" should be -- May 7, 2020 --.

Signed and Sealed this
Nineteenth Day of March, 2024

*Katherine Kelly Vidal*

Katherine Kelly Vidal
*Director of the United States Patent and Trademark Office*